(12) United States Patent
Malinowski et al.

(10) Patent No.: US 7,595,380 B2
(45) Date of Patent: Sep. 29, 2009

(54) MONOCLONAL ANTIBODIES AND METHODS FOR THEIR USE IN THE DETECTION OF CERVICAL DISEASE

(75) Inventors: Douglas P. Malinowski, Hillsborough, NC (US); Timothy J. Fischer, Raleigh, NC (US); Adriann J. Taylor, Durham, NC (US)

(73) Assignee: TriPath Imaging, Inc., Burlington, NC (US)

( * ) Notice: Subject to any disclaimer, the term of this patent is extended or adjusted under 35 U.S.C. 154(b) by 0 days.

(21) Appl. No.: 11/410,272

(22) Filed: Apr. 24, 2006

(65) Prior Publication Data

US 2006/0252106 A1 Nov. 9, 2006

Related U.S. Application Data

(60) Provisional application No. 60/675,305, filed on Apr. 27, 2005, provisional application No. 60/718,082, filed on Sep. 16, 2005.

(51) Int. Cl.
*C07K 16/00* (2006.01)
*A61K 38/00* (2006.01)

(52) U.S. Cl. ............... 530/388.1; 530/387.9; 530/388.8

(58) Field of Classification Search ................. None
See application file for complete search history.

(56) References Cited

U.S. PATENT DOCUMENTS

| 4,281,061 A * | 7/1981 | Zuk et al. ............... 435/7.9 |
| 7,157,233 B2 * | 1/2007 | Fischer et al. ............ 435/6 |
| 2005/0250166 A1 * | 11/2005 | Masai et al. ............ 435/15 |
| 2005/0260566 A1 * | 11/2005 | Fischer et al. ............ 435/5 |

FOREIGN PATENT DOCUMENTS

| EP | 1 388 734 A1 | 2/2004 |
| EP | 1 489 177 A1 | 12/2004 |
| WO | 03/76623 * | 9/2003 |
| WO | WO 2005/095964 A2 | 10/2005 |

OTHER PUBLICATIONS

Rudikoff, S., Giusti, A.M., Cook, W.D., and Scharff, M.D. Single amino acid substitution altering antigen-binding specificity. 1982. Proceedings of the National Academy of Sciences, vol. 79 pp. 1979-1983.*
Panka, D.J., Mudgett-Hunter, M., Parks, D.R., Peterson, L.L., Herzenberg, L.A., Haber, E., and Margolies, M.N. Variable region framework differences result in decreased or increased affinity of variant anti-digoxin antibodies. 1988. Proceedings of the National Academy of Sciences, vol. 85, pp. 3080-3084.*
Burgess, Shaheen, Ravera, Jaaye, Donohue, and Winkles. Possible dissociation of the heparin-binding and mitogenic activites of heparin-binding (acidic fibroblast) growth factor-1 from its receptor-binding activites by site-directed mutagenesis of a single lysine residue. Journal of Cell Biology, 1990. vol. 111, pp. 2129-2138.*
Lazar, E., Watanabe, S., Dalton, S., and Sporn, M.B. Transforming growth factor a: mutation of aspartic acid 47 and leucine 48 results in different biological activites. Molecular and Cellular Biology, 1988. vol. 8 No. 3, pp. 1247-1252.*
Schwartz, G., Burke, G.T., and Katsoyannis, P.G. A superactive insulin: [B10-aspartic acid] insulin (human). Proceedings of the National Academy of Sciences, 1987. vol. 84, pp. 6408-6411.*
Lin, M.C., Wright, D.E., Hruby, V.J., and Rodbell, M. Structure-function relationships in glucagon: properties of highly purified Des-His1- Monoiodo-, and [Des-Asn28, Thr29] (homoserine lactone 27)-glucagon. Biochemistry, 1975. vol. 14 No. 8, pp. 1559-1563.*
Campbell, Monoclonal Antibody Technology, Eds. Elsevier, Chapter 1, pp. 1-32 (1984).*
Brake, T., et al., "Comparative Analysis of Cervical Cancer in Women and in a Human Papillomavirus-Transgenic Mouse Model: Identification of *Minichromosome Maintenance Protein 7*," *Cancer Research*, 2003, pp. 8173-8180, vol. 63.
Freeman, A., et al., "Minichromosome Maintenance Proteins as Biological Markers of Dysplasia and Malignancy", *Clinical Cancer Research*, 1999, pp. 2121-2132, vol. 5.
Going, J.J., et al., Aberrant Expression of Minichromosome Maintenance Proteins 2 and 5, and Ki-67 in Dysplastic Squamous Oesophageal Epithelium and Barrett's Mucosa, Cancer, 2006, pp. 373-377, vol. 50.
Krüger, S., et at., Prognostic Value of MCM2 Immunoreactivity in Stage T1 Transitional Cell Carcinoma of the Bladder, *European Urology*, 2003, pp. 138-145, vol. 43.
Malinowski, D.P., "Molecular Diagnostic Assays for Cevical Neoplasia: Emerging Markers for the Detection of High-Grade Cervical Disease," *Biotechiques*, 2005, pp. 17-23, vol. 38.
Mukherjee, G., et al., "Biologic Factors and Response to Radiotherapy in Carcinoma of the Cervix," *Int. J. Gynecol. Cancer*, 2001, pp. 187-193, vol. 11.
Mushika, M. et al., "Detection of Proliferative Cells in Dysplasia, Carcinoma In Situ, and Invasive Carcinoma of the uterine Cervix by Monoclonal Antibody Against DNA Polymerase α," *Cancer*, 1998, pp. 1182-1186, vol. 61.

(Continued)

*Primary Examiner*—Sheela J Huff
(74) *Attorney, Agent, or Firm*—Alston & Bird LLP

(57) ABSTRACT

Compositions and methods for diagnosing high-grade cervical disease in a patient sample are provided. The compositions include novel monoclonal antibodies, and variants and fragments thereof, that specifically bind to MCM2. Monoclonal antibodies having the binding characteristics of an MCM2 antibody of the invention are further provided. Hybridoma cell lines that produce an MCM2 monoclonal antibody of the invention are also disclosed herein. The compositions find use in practicing methods for diagnosing high-grade cervical disease comprising detecting overexpression of MCM2 in a cervical sample from a patient. Kits for practicing the methods of the invention are further provided. Polypeptides comprising the amino acid sequence for an MCM2 epitope and methods of using these polypeptides in the production of antibodies are also encompassed by the present invention.

14 Claims, No Drawings

OTHER PUBLICATIONS

Tan, D.-F., et al., "MCM2-A Promising Marker for Premalignant Lesions of the Lung: A Cohort Study," *BMC Cancer*, 2001, pp. 6-12, vol. 1(6).

Product Data Sheet for ab6I53, URL: htpp://www.abcam.com/index.html:pageconfig=datasheet&intABID=6153>, Oct. 11, 2000, pp. 1-3.

Product Data Sheet for 17788, URL: htpp://www.abcam.com/index.html?pageconfig=datasheet&intABID=17788>, Mar. 2, 2005, pp. 1-3.

Data Sheet for Minichromosome Maintenance Protein 2, NCL-MCM2, URL:htpp://www.vision-bio.com/pdfs/products/mcm2-u.pdf, Nov. 13, 2006, pp. 1-2.

* cited by examiner

MONOCLONAL ANTIBODIES AND METHODS FOR THEIR USE IN THE DETECTION OF CERVICAL DISEASE

CROSS REFERENCE TO RELATED APPLICATIONS

This application claims the benefit of U.S. Provisional Application Ser. No. 60/675,305, filed Apr. 27, 2005, and U.S. Provisional Application Ser. No. 60/718,082, filed Sep. 16, 2005, both of which are incorporated herein by reference in their entirety.

FIELD OF THE INVENTION

The invention relates to antibodies capable of binding to MCM2 and methods of using these antibodies, particularly in the diagnosis of cervical disease.

BACKGROUND OF THE INVENTION

Carcinoma of the cervix is the second most common neoplasm in women, accounting for approximately 12% of all female cancers and causing approximately 250,000 deaths per year. Baldwin et al. (2003) *Nature Reviews Cancer* 3:1-10. In many developing countries where mass screening programs are not available, the clinical problem is more serious. Cervical cancer in these countries is the number one cause of cancer deaths in women.

The majority of cases of cervical cancer represent squamous cell carcinoma, although adenocarcinoma is also seen. Cervical cancer can be prevented by population screening as it evolves through well-defined noninvasive intraepithelial stages, which can be distinguished morphologically. Williams et al. (1998) *Proc. Natl. Acad. Sci. USA* 95:14932-14937. While it is not understood how normal cells become transformed, the concept of a continuous spectrum of histopathological change from normal, stratified epithelium through cervical intraepithelial neoplasia (CIN) to invasive cancer has been widely accepted for years. The precursor to cervical cancer is dysplasia, also known in the art as CIN or squamous intraepithelial lesions (SIL). Squamous intraepithelial abnormalities may be classified by using the three-tiered (CIN) or two-tiered (Bethesda) system. Under the Bethesda system, low-grade squamous intraepithelial lesions (LSIL), corresponding to CINI and HPV infection, generally represent productive HPV infections with a relatively low risk of progression to invasive disease. High-grade squamous intraepithelial lesions (HSIL), corresponding to CINII and CINIII in the three-tiered system, show a higher risk of progression to cervical cancer than do LSIL, although both LSIL and HSIL are viewed as potential precursors of malignancy. Patient samples may also be classified as ASCUS (atypical squamous cells of unknown significance) or AGUS (atypical glandular cells of unknown significance) under this system.

A strong association of cervical cancer and infection by high-risk types of human papilloma virus (HPV), such as types 16, 18, and 31, has been established. In fact, a large body of epidemiological and molecular biological evidence has established HPV infection as a causative factor in cervical cancer. Moreover, HPV is found in 85% or more of the cases of high-grade cervical disease. However, HPV infection is very common, possibly occurring in 5-15% of women over the age of 30, but few HPV-positive women will ever develop high-grade cervical disease or cancer. The presence of HPV alone is indicative only of infection, not of high-grade cervical disease, and, therefore, testing for HPV infection alone results in many false positives. See, for example, Wright et al. (2004) *Obstet. Gynecol.* 103:304-309.

Current literature suggests that HPV infects the basal stem cells within the underlying tissue of the uterine-cervix. Differentiation of the stem cells into mature keratinocytes, with resulting migration of the cells to the stratified cervical epithelium, is associated with HPV viral replication and re-infection of cells. During this viral replication process, a number of cellular changes occur that include cell-cycle de-regulation, active proliferation, DNA replication, transcriptional activation and genomic instability (Crum (2000) *Modern Pathology* 13:243-251; Middleton et al. (2003) *J. Virol.* 77:10186-10201; Pett et al. (2004) *Cancer Res.* 64:1359-1368).

Most HPV infections are transient in nature, with the viral infection resolving itself within a 12-month period. For those individuals who develop persistent infections with one or more oncogenic subtypes of HPV, there is a risk for the development of neoplasia in comparison to patients without an HPV infection. Given the importance of HPV in the development of cervical neoplasia, the clinical detection of HPV has become an important diagnostic tool in the identification of patients at risk for cervical neoplasia development. The clinical utility of HPV-based screening for cervical disease is in its negative predictive value. An HPV negative result in combination with a history of normal Pap smears is an excellent indicator of a disease-free condition and a low risk of cervical neoplasia development during the subsequent 1-3 years. However, a positive HPV result is not diagnostic of cervical disease; rather it is an indication of infection. Although the majority of HPV infections is transient and will spontaneously clear within a 12-month period, a persistent infection with a high-risk HPV viral subtype indicates a higher risk for the development of cervical neoplasia. To supplement HPV testing, the identification of molecular markers associated with cervical neoplasia is expected to improve the clinical specificity for cervical disease diagnosis.

Cytological examination of Papanicolaou-stained cervical smears (Pap smears) currently is the method of choice for detecting cervical cancer. The Pap test is a subjective method that has remained substantially unchanged for 60 years. There are several concerns, however, regarding its performance. The reported sensitivity of a single Pap test (the proportion of disease positives that are test-positive) is low and shows wide variation (30-87%). The specificity of a single Pap test (the proportion of disease negatives that are test-negative) might be as low as 86% in a screening population and considerably lower in the ASCUS PLUS population for the determination of underlying high-grade disease. See, Baldwin et al., supra. A significant percentage of Pap smears characterized as LSIL or CINI are actually positive for high-grade lesions. Furthermore, up to 10% of Pap smears are classified as ASCUS (atypical squamous cells of undetermined significance), i.e., it is not possible to make a clear categorization as normal, moderate or severe lesion, or tumor. However, experience shows that up to 10% of this ASCUS population has high-grade lesions, which are consequently overlooked. See, for example, Manos et al. (1999) *JAMA* 281:1605-1610. Therefore, molecular biomarkers that are selectively overexpressed in high-grade cervical disease and compositions for the detection of these biomarkers are needed to practice reliable methods for diagnosing high-grade cervical disease.

Minichromosome maintenance (MCM) proteins play an essential part in eukaryotic DNA replication. The minichromosome maintenance (MCM) proteins function in the early stages of DNA replication through loading of the prereplication complex onto DNA and functioning as a helicase to help unwind the duplex DNA during de novo synthesis of the duplicate DNA strand. Each of the MCM proteins has DNA-dependent ATPase motifs in their highly conserved central domain. Levels of MCM proteins generally increase in a variable manner as normal cells progress from G0 into the G1/S phase of the cell cycle. In the G0 phase, MCM2 and MCM5 proteins are much less abundant than are the MCM7 and MCM3 proteins. MCM6 forms a complex with MCM2, MCM4, and MCM7, which binds histone H3. In addition, the subcomplex of MCM4, MCM6, and MCM7 has helicase activity, which is mediated by the ATP-binding activity of MCM6 and the DNA-binding activity of MCM4. See, for example, Freeman et al. (1999) Clin. Cancer Res. 5:2121-2132; Lei et al. (2001) J. Cell Sci. 114:1447-1454; Ishimi et al. (2003) Eur. J. Biochem. 270:1089-1101, all of which are herein incorporated by reference in their entirety.

Early publications have shown that the MCM proteins, and in particular, MCM-5, are useful for the detection of cervical disease (Williams et al. (1998) Proc Natl Acad Sci U.S.A. 95:14932-14937), as well as other cancers (Freeman et al. (1999) Clin Cancer Res. 5:2121-2132). The published literature indicates that antibodies to MCM-5 are capable of detecting cervical neoplastic cells. The specificity for detection of high-grade cervical disease has not been demonstrated for MCM-5 (Williams et al. (1998) Proc Natl Acad Sci U.S.A. 95:14932-14937). The detection of MCM-5 expression is not restricted to high-grade cervical disease but is also detected in identified low-grade dysplasia and proliferative cells that have re-entered the cell cycle following infection with high-risk HPV. In addition to MCM-5, other members from the MCM family, including MCM-2 and MCM-7 have been shown to be potentially useful markers for the detection of cervical neoplasia in tissue samples (Freeman et al. (1999) Clin Cancer Res. 5:2121-2132; Brake et al. (2003) Cancer Res. 63:8173-8180). Recent results have shown that MCM-7 appears to be a specific marker for the detection of high-grade cervical disease using immunochemistry formats (Brake et al. (2003) Cancer Res. 63:8173-8180; Malinowski et al. (2004) Acta Cytol. 43:696).

Therefore, there is a need in the art for antibodies that are capable of detecting expression of a biomarker that is selectively overexpressed in high-grade cervical disease. Such antibodies could be used in methods for differentiating high-grade disease from conditions that are not considered clinical disease, such as early-stage HPV infection and mild dysplasia.

SUMMARY OF THE INVENTION

Compositions and methods for diagnosing high-grade cervical disease are provided. Compositions include monoclonal antibodies capable of binding to nuclear biomarker proteins of the invention, particularly MCM proteins, more particularly MCM2. Antigen-binding fragments and variants of these monoclonal antibodies, hybridoma cell lines capable of producing these antibodies, and kits comprising the monoclonal antibodies of the invention are also encompassed herein.

The compositions of the invention find use in methods for diagnosing high-grade cervical disease. The methods comprise detecting overexpression of at least one nuclear biomarker, wherein overexpression of the nuclear biomarker is indicative of high-grade cervical disease. Specifically, the methods comprise using the antibodies of the invention to detect overexpression of MCM2 in a cervical sample.

Compositions of the invention further include isolated polypeptides that comprise an epitope capable of binding an MCM2 monoclonal antibody. These polypeptides find use in methods for producing MCM2 antibodies. Isolated nucleic acid molecules encoding the amino acid sequences of the MCM2 epitopes are also provided.

DETAILED DESCRIPTION OF THE INVENTION

Compositions and methods for diagnosing high-grade cervical disease are provided. Compositions include monoclonal antibodies that are capable of binding to nuclear biomarker proteins that are selectively overexpressed in high-grade cervical disease, particularly MCM proteins, more particularly MCM2. Hybridoma cell lines that produce the monoclonal antibodies of the present invention are also disclosed. Kits comprising the monoclonal antibodies described herein are further provided. The present compositions find use in methods for diagnosing high-grade cervical disease in a patient.

The compositions of the invention include monoclonal antibodies that specifically bind to MCM2, or to a variant or fragment thereof. In particular, the MCM2 antibodies designated as 27C5.6 and 26H6.19 are provided. Hybridoma cell lines that produce MCM2 monoclonal antibodies 27C5.6 and 26H6.19 were deposited with the Patent Depository of the American Type Culture Collection (ATCC), Manassas, Va., 20110-2209 on Apr. 14, 2005 and assigned Patent Deposit Nos. PTA-6668 and PTA-6667, respectively. These deposits will be maintained under the terms of the Budapest Treaty on the International Recognition of the Deposit of Microorganisms for the Purposes of Patent Procedure. Upon issuance of a patent, Applicants hereby provide assurances that all restrictions on the accessibility of the above-referenced deposited hybridomas will be irrevocably removed. These deposits were made merely as a convenience for those of skill in the art and are not an admission that a deposit is required under 35 U.S.C. § 112.

Antibodies that have the binding characteristics of monoclonal antibodies 27C5.6, and 26H6.19 are also disclosed herein. Such antibodies include, but are not limited to, antibodies that compete in competitive binding assays with these antibodies, as well as antibodies that bind to an epitope capable of binding monoclonal antibody 27C5.6 or 26H6.19. Variants and fragments of monoclonal antibodies 27C5.6 and 26H6.19 that retain the ability to specifically bind to MCM2 are also provided. Compositions further include hybridoma cell lines that produce the monoclonal antibodies of the present invention and kits comprising at least one monoclonal antibody disclosed herein.

"Antibodies" and "immunoglobulins" (Igs) are glycoproteins having the same structural characteristics. While antibodies exhibit binding specificity to an antigen, immunoglobulins include both antibodies and other antibody-like molecules that lack antigen specificity. Polypeptides of the latter kind are, for example, produced at low levels by the lymph system and at increased levels by myelomas.

The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site. Antibody derivatives may comprise a protein or chemical moiety conjugated to the antibody. The term "antibody" is used in the broadest sense and covers fully assembled antibodies, antibody fragments that can bind antigen (e.g., Fab', F'(ab)$_2$, Fv, single chain antibodies, diabodies), and recombinant peptides comprising the foregoing. As used herein, "MCM2 antibody" refers to any antibody that specifically binds to MCM2

(SEQ ID NO:1), or to a variant or fragment thereof, and includes monoclonal antibodies, polyclonal antibodies, single-chain antibodies, and fragments thereof which retain the antigen binding function of the parent antibody.

The MCM2 antibodies of the invention are optimally monoclonal antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (V,) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity determining regions (CDRs) or hypervariable regions both in the light chain and the heavy-chain variable domains. The more highly conserved portions of variable domains are called the framework (FR) regions. The variable domains of native heavy and light chains each comprise four FR regions, largely adopting a p-sheet configuration, connected by three CDRs, which form loops connecting, and 15 in some cases forming part of, the p-sheet structure. The CDRs in each chain are held together in close proximity: by the FR regions and, with the CDRs from the other chain, contribute to the formation of the antigen-binding site: of antibodies (see Kabat et al., NIH Publ. No. 91-3242, Vol. I, pages 647-669 (1991)).

The constant domains are not involved directly in binding an antibody to an antigen, but exhibit various effecter functions, such as participation of the antibody in antibody-dependent cellular toxicity.

The term "hypervariable region" when used herein refers to the amino acid residues of an antibody which: are responsible for antigen-binding. The hypervariable region comprises amino acid residues from a "complementarily determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institute of Health, i 25 Bethesda, Md. [1991]) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Clothia and Lesk, J. Mol. Biol., 196:901-917 [1987]). "Framework" or "FR" residues are those variable domain residues other than the hypervariable region residues as herein deemed.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) *Protein Eng.* 8(10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them.

Fragments of the MCM2 antibodies are encompassed by the invention so long as they retain the desired affinity of the full-length antibody. Thus, for example, a fragment of an MCM2 antibody will retain the ability to bind to the MCM2 antigen. Such fragments are characterized by properties similar to the corresponding full-length antibody, that is, the fragments will specifically bind MCM2. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, F(ab')$_2$, and Fv fragments and single-chain antibody molecules. By "Fab" is intended a monovalent antigen-binding fragment of an immunoglobulin that is composed of the light chain and part of the heavy chain. By F(ab')$_2$ is intended a bivalent antigen-binding fragment of an immunoglobulin that contains both light chains and part of both heavy chains. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the $V_H$ and $V_L$ domains that enables the sFv to form the desired structure for antigen binding. For a review of sFv see Pluckthun (1994) in *The Pharmacology of Monoclonal Antibodies*, Vol. 113, ed. Rosenburg and Moore (Springer-Verlag, N.Y. ), pp. 269-315.

Antibodies or antibody fragments can be isolated from antibody phage libraries generated using the techniques described in, for example, McCafferty et al. (1990) *Nature* 348:552-554 (1990) and U.S. Pat. No. 5,514,548. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. (1992) *Bio/Technology* 10:163-167). According to another approach, F(ab')$_2$ fragments can be isolated directly from recombinant host cell culture. Other techniques for the production of antibody fragments will be apparent to the skilled practitioner.

Preferably antibodies of the invention are monoclonal in nature. As indicated above, "monoclonal antibody" is intended an antibody obtained from a population of substantially homogeneous antibodies, i.e., the individual antibodies comprising the population are identical except for possible naturally occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site, i.e., a particular epitope within the MCM2 protein, as defined herein below. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in, for example, Clackson et al. (1991) *Nature* 352:624-628; Marks et al. (1991) *J. Mol. Biol.* 222:581-597; and U.S. Pat. No. 5,514,548.

Monoclonal antibodies can be prepared using the method of Kohler et al. (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen (i.e., antibody-producing cells) bind to the plate and are not rinsed away. Resulting B cells, or all dissociated spleen cells, are then induced to fuse with myeloma cells to form monoclonal antibody-producing hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice). Monoclonal antibodies can also be produced using Repetitive Immunizations Multiple Sites technology (RIMMS). See, for example, Kilpatrick et al. (1997) *Hybridoma* 16(4):381-389; Wring et al. (1999) *J. Pharm. Biomed. Anal.* 19(5):695-707; and Bynum et al. (1999) *Hybridoma* 18(5):407-411, all of which are herein incorporated by reference in their entirety.

As an alternative to the use of hybridomas, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody. A monoclonal antibody can also be identified and isolated by screening a recombinant combinatorial immunoglobulin library (e.g., an antibody phage display library) with a biomarker protein to thereby isolate immunoglobulin library members that bind the biomarker protein. Kits for generating and screening phage display libraries are commercially available (e.g., the Pharmacia *Recombinant Phage Antibody System*, Catalog No. 27-9400-01; and the Stratagene SurfZAP⇔Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

In some aspects of the invention, antibodies may be selected on the basis of desirable staining of cytological, rather than histological, samples. That is, in particular embodiments the antibodies are selected with the end sample type (e.g., cytology preparations) in mind and for binding specificity. Antibodies directed to specific biomarkers of interest, such as MCM2, are selected and purified via a multistep screening process. Such methods for antibody selection are described in pending U.S. application Ser. No. 11/087,227, entitled "Methods and Compositions for the Detection of Cervical Disease," filed Mar. 23, 2005, which is herein incorporated by reference in its entirety.

Antibodies having the binding characteristics of a monoclonal antibody of the invention are also provided. "Binding characteristics" or "binding specificity" when used in reference to an antibody means that the antibody recognizes the same or similar antigenic epitope as a comparison antibody. Examples of such antibodies include, for example, an antibody that competes with a monoclonal antibody of the invention in a competitive binding assay. One of skill in the art could determine whether an antibody competitively interferes with another antibody using standard methods.

By "epitope" is intended the part of an antigenic molecule to which an antibody is produced and to which the antibody will bind. An "MCM2 epitope" comprises the part of the MCM2 protein to which an MCM2 monoclonal antibody binds. Epitopes can comprise linear amino acid residues (i.e., residues within the epitope are arranged sequentially one after another in a linear fashion), nonlinear amino acid residues (referred to herein as "nonlinear epitopes"; these epitopes are not arranged sequentially), or both linear and nonlinear amino acid residues. Typically epitopes are short amino acid sequences, e.g. about five amino acids in length. Systematic techniques for identifying epitopes are known in the art and are described, for example, in U.S. Pat. No. 4,708,871 and in the examples set forth below. Briefly, in one method, a set of overlapping oligopeptides derived from the antigen may be synthesized and bound to a solid phase array of pins, with a unique oligopeptide on each pin. The array of pins may comprise a 96-well microtiter plate, permitting one to assay all 96 oligopeptides simultaneously, e.g., for binding to a biomarker-specific monoclonal antibody. Alternatively, phage display peptide library kits (New England BioLabs) are currently commercially available for epitope mapping. Using these methods, the binding affinity for every possible subset of consecutive amino acids may be determined in order to identify the epitope that a given antibody binds. Epitopes may also be identified by inference when epitope length peptide sequences are used to immunize animals from which antibodies are obtained.

The invention also encompasses isolated polypeptides comprising an epitope for binding an MCM2 monoclonal antibody. These polypeptides correspond to a portion of the antigen (i.e., MCM2) that binds to a monoclonal antibody. Such polypeptides find use in methods for producing antibodies that bind selectively to MCM2. The ability of a polypeptide to be used in the production of antibodies is referred to herein as "antigenic activity." For example, the amino acid sequences set forth in SEQ ID NOs: 3, 4, and 14 (corresponding to residues 369 to 382, 688 to 710, and 683 to 692, respectively, in the MCM2 amino acid sequence set forth in SEQ ID NO:1) comprise epitopes recognized by MCM2 monoclonal antibodies, more particularly monoclonal antibodies 27C5.6 and 26H6.19. See Example 4 for details. Variants and fragments of the MCM2 epitope sequences set forth in SEQ ID NOs: 3, 4, and 14 that retain the antigenic activity of the original polypeptide are also provided. The invention further includes isolated nucleic acid molecules that encode polypeptides that comprise MCM2 epitopes, and variants and fragments thereof.

The polypeptides of the invention comprising MCM2 epitopes can be used in methods for producing monoclonal antibodies that specifically bind to MCM2, as described herein above. Such polypeptides can also be used in the production of polyclonal MCM2 antibodies. For example, polyclonal antibodies can be prepared by immunizing a suitable subject (e.g., rabbit, goat, mouse, or other mammal) with a polypeptide comprising an MCM2 epitope (i.e., an immunogen). The antibody titer in the immunized subject can be monitored over time by standard techniques, such as with an enzyme linked immunosorbent assay (ELISA) using immobilized biomarker protein. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387-402).

Amino acid sequence variants of a monoclonal antibody or a polypeptide comprising an MCM2 epitope described herein are also encompassed by the present invention. Variants can be prepared by mutations in the cloned DNA sequence encoding the antibody of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the polypeptide of interest, modifications are made such that variants continue to possess the desired activity, i.e., similar binding affinity to the biomarker. Obviously, any mutations made in the DNA encoding the variant polypeptide must not place the sequence out of reading frame and preferably will not create complementary regions that could produce secondary mRNA structure. See EP Patent Application Publication No. 75,444.

Preferably, variants of a reference polypeptide have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference antibody molecule, or to a shorter portion of the reference antibody molecule. More preferably, the molecules share at least 96%, 97%, 98% or 99% sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference antibody by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

The MCM2 monoclonal antibodies of the invention may be labeled with a detectable substance as described below to facilitate biomarker protein detection in the sample. Such antibodies find use in practicing the methods of the invention. The antibodies and antibody fragments of the invention can be coupled to a detectable substance to facilitate detection of antibody binding. The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Examples of detectable substances for purposes of labeling antibodies include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Kits comprising at least one MCM2 monoclonal antibody of the invention are further provided. By "kit" is intended any manufacture (e.g., a package or a container) comprising at least one reagent, i.e., an antibody, for specifically detecting the expression of MCM2. The kit may be promoted, distributed, or sold as a unit for performing the methods of the present invention. Additionally, the kits may contain a package insert describing the kit and methods for its use.

Kits of the invention generally comprise at least one monoclonal antibody directed to MCM2, chemicals for the detection of antibody binding, a counterstain, and, optionally, a bluing agent to facilitate identification of positive staining cells. Any chemicals that detect antigen-antibody binding may be used in the kits of the invention. In some embodiments, the detection chemicals comprise a labeled polymer conjugated to a secondary antibody. For example, a secondary antibody that is conjugated to an enzyme that catalyzes the deposition of a chromogen at the antigen-antibody binding site may be provided. Such enzymes and techniques for using them in the detection of antibody binding are well known in the art. In one embodiment, the kit comprises a secondary antibody that is conjugated to an HRP-labeled polymer. Chromogens compatible with the conjugated enzyme (e.g., DAB in the case of an HRP-labeled secondary antibody) and solutions, such as hydrogen peroxide, for blocking non-specific staining may be further provided. In other embodiments, antibody binding to a biomarker protein is detected through the use of a mouse probe reagent that binds to monoclonal antibodies, followed by addition of a dextran polymer conjugated with HRP that binds to the mouse probe reagent. Such detection reagents are commercially available from, for example, Biocare Medical.

The kits of the present invention may further comprise a peroxidase blocking reagent (e.g., hydrogen peroxide), a protein blocking reagent (e.g., purified casein), and a counterstain (e.g., hematoxylin). A bluing agent (e.g., ammonium hydroxide or TBS, pH 7.4, with Tween-20 and sodium azide) may be further provided in the kit to facilitate detection of positive staining cells. Kits may also comprise positive and negative control samples for quality control purposes.

In another embodiment, the kits of the invention comprise two MCM2 monoclonal antibodies, more particularly monoclonal antibodies 27C5.6 and 26H6.19. A kit comprising two MCM2 monoclonal antibodies and a third antibody directed to topoisomerase II alpha (Topo2A) is further provided. When multiple antibodies are present in the kit, each antibody may be provided as an individual reagent or, alternatively, as an antibody cocktail comprising all of the antibodies of interest. Furthermore, any or all of the kit reagents may be provided within containers that protect them from the external environment, such as in sealed containers. The kits of the invention are useful in the diagnosis of high-grade cervical disease and may further include reagents for Pap staining (e.g., EA50 and Orange G).

The compositions of the invention find use in methods for diagnosing high-grade cervical disease in a patient such as those disclosed in pending U.S. application Ser. No. 11/087,227, entitled "Methods and Compositions for the Detection of Cervical Disease," filed Mar. 23, 2005, which is herein incorporated by reference in its entirety. "Diagnosing high-grade cervical disease" is intended to include, for example, diagnosing or detecting the presence of cervical disease, monitoring the progression of the disease, and identifying or detecting cells or samples that are indicative of high-grade cervical disease. The terms diagnosing, detecting, and identifying high-grade cervical disease are used interchangeably herein. By "high-grade cervical disease" is intended those conditions classified by colposcopy as premalignant pathology, malignant pathology, moderate to severe dysplasia, and cervical cancer. Underlying high-grade cervical disease includes histological identification of CINII, CINIII, HSIL, carcinoma in situ, adenocarcinoma, and cancer (FIGO stages I-IV).

The methods of the invention comprise detecting overexpression of at least one nuclear biomarker that is selectively overexpressed in high-grade cervical disease. By "nuclear biomarker" is intended any gene of protein that is predominantly expressed in the nucleus of the cell. A nuclear biomarker may be expressed to a lesser degree in other parts of the cell. By "selectively overexpressed in high-grade cervical disease" is intended that the nuclear biomarker of interest is overexpressed in high-grade cervical disease but is not overexpressed in conditions classified as LSIL, CINI, HPV-infected samples without any dysplasia present, immature metaplastic cells, and other conditions that are not considered to be clinical disease. Thus, detection of the nuclear biomarkers of the invention permits the differentiation of samples indicative of underlying high-grade cervical disease from samples that are indicative of benign proliferation, early-stage HPV infection, or mild dysplasia. Nuclear biomarkers of particular interest include MCM proteins, particularly MCM2, and Topo2A.

In a particular aspect of the invention, the methods comprise obtaining a cervical sample from a patient, contacting the sample with at least one MCM2 monoclonal antibody of the invention, and detecting binding of the antibody to MCM2. In other embodiments, the sample is contacted with at least two monoclonal antibodies that specifically bind to MCM2, particularly monoclonal antibodies 27C5.6 and 26H6.19. In a further embodiment, the sample is contacted with these two MCM2 monoclonal antibodies and a third antibody that specifically binds to Topo2A. Techniques for detecting antibody binding are well known in the art. Antibody binding to a biomarker of interest may be detected through the use of chemical reagents that generate a detectable signal that corresponds to the level of antibody binding and, accordingly, to the level of biomarker protein expression. Any method for detecting antibody-antigen binding may used to practice the methods of the invention.

As used herein, "cervical sample" refers to any sampling of cells, tissues, or bodily fluids from the cervix in which expression of a biomarker can be detected. Examples of such body samples include but are not limited to gynecological fluids, biopsies, and smears. Cervical samples may be obtained from a patient by a variety of techniques including, for example, by scraping or swabbing an area or by using a needle to aspirate bodily fluids. Methods for collecting cervical samples are well known in the art. In particular embodiments, the cervical sample comprises cervical cells, particularly in a liquid-based preparation. In one embodiment, cervical samples are collected according to liquid-based cytology specimen preparation guidelines such as, for example, the SUREPATH® (TriPath Imaging, Inc.) or the THINPREP® preparation (CYTYC, Inc.). Cervical samples may be transferred to a glass slide for viewing under magnification. Fixative and staining solutions may be applied to the cells on the glass slide for preserving the specimen and for facilitating examination. In one embodiment the cervical sample will be collected and processed to provide a monolayer sample, as set forth in U.S. Pat. No. 5,346,831, herein incorporated by reference.

One of skill in the art will appreciate that any or all of the steps in the methods of the invention could be implemented by personnel in a manual or automated fashion. Thus, the steps of cervical sample preparation, antibody, and detection of antibody binding may be automated. The methods of the invention may also be combined with conventional Pap staining techniques to permit a more accurate diagnosis of high-grade cervical disease.

The following examples are offered by way of illustration and not by way of limitation:

EXPERIMENTAL

Example 1

Production of Mouse Monoclonal Antibodies to MCM2

Mouse monoclonal antibodies specific for MCM2 were generated. The antigen (an immunogenic polypeptide) was a full-length recombinant hexahistidine-tagged MCM2 protein. The antigen was expressed using a baculovirus expression system in Tni cells. Specifically, the coding sequence for the hexahistidine-tagged MCM2 (SEQ ID NO:10) was cloned into the pFastBac1 plasmid (Invitrogen) for expression in Tni cells. Methods for producing recombinant proteins using baculovirus expression systems are well known in the art. The tagged MCM2 protein was purified using a chelating agarose charged with Ni+2 ions (Ni-NTA from Qiagen) and used as an immunogen. The amino acid sequence of the immunogenic MCM2 polypeptide is provided in SEQ ID NO:11.

Mouse immunizations and hybridoma fusions were performed essentially as described in Kohler et al. (1975) *Nature* 256:495-496. Mice were immunized with the immunogenic tagged-MCM2 protein in solution. Antibody-producing cells were isolated from the immunized mice and fused with myeloma cells to form monoclonal antibody-producing hybridomas. The hybridomas were cultured in a selective medium. The resulting cells were plated by serial dilution and assayed for the production of antibodies that specifically bind MCM2 (and that do not bind to unrelated antigens). To confirm that the monoclonal antibodies of interest reacted with the MCM2 protein only and not with the hexahistidine tag, selected hybridomas were screened against an MCM2-FLAG-tagged protein. The nucleotide and amino acid sequences for the MCM2-FLAG protein are set forth in SEQ ID NOs:12 and 13, respectively. Selected monoclonal antibody (mAb)-secreting hybridomas were then cultured.

Antibodies were purified from the culture media supernatants of "exhausted" hybridoma cells (i.e., cells grown until viability drops to between 0-15%) using recombinant Protein A-coated resin (STREAMLINE®, Amersham, Inc.). Antibodies were eluted using low pH followed by immediate neutralization of pH. Fractions with significant absorbances at 280 nM were pooled. The resultant pool was dialyzed against PBS. Purified antibodies were subjected to further characterization. MCM2 monoclonal antibodies 26H6.19 and 27C5.6 were both determined to be $IgG_1$ isotypes. Details of the epitope mapping of these antibodies are described below.

Example 2

Isolation of Monoclonal Antibodies from Hybridoma Cells

The following procedure is used to isolate monoclonal antibodies from hybridoma cells:

Media Preparation
  To a sterile 1,000 ml storage bottle, add 100 ml Hyclone Fetal Bovine Serum (FBS).
  Add 10 ml of MEM Non-Essential Amino Acids Solution.
  Add 10 ml of Penicillin-Streptomycin-L-Glutamine Solution.
  QS to approximately 1000 ml with ExCell 610-HSF media.
  Place sterile cap on bottle and secure tightly. Swirl gently to mix.
  Connect a 1000 ml sterile acetate vacuum filter unit (0.2 μm) to a vacuum pump system.
  Gently pour approximately half of the media solution into sterile acetate vacuum filter unit and turn on the vacuum.
  Once the first half of the media has been filtered, pour the remaining media into the filter unit and continue filtering.
  After all the media has been filtered, disconnect the vacuum hose from the vacuum filter unit and turn off the vacuum pump. Remove the receiver portion of the filter unit from the filter bottle. Place a new sterile bottle cap on the bottle.
  Store at 2° C. to 10° C. Protect from light.

Initial Hybridoma Cell Culture
  Thaw vial of stock hybridoma frozen culture in a pre-warmed 37° C. $H_2O$ bath.
  Spray the outside of the freeze vial with 70% ethanol.
  Move the thawed vial into the Biological Safety Cabinet.
  Remove the cells from the freeze vial and transfer the cells to a 15 ml centrifuge tube.

Add 7 ml of cell culture media drop-wise to the 15 ml centrifuge tube containing the thawed cells.

Centrifuge the 15 ml centrifuge tube containing the thawed cells and culture media for 5 minutes at 200 g force.

While the cells are in the centrifuge, add 45 ml of cell culture media to a sterile T-225 flask.

After centrifugation, visually inspect the tube for the presence of a cell pellet.

Remove the media from the centrifuge tube being careful not to dislodge the cell pellet. Note: If the cell pellet is disturbed, repeat the centrifugation step.

Add 5 ml of cell culture media to the 15 ml centrifuge tube containing the pelleted cells. Pipette to re-suspend the cell pellet into the media.

Transfer the entire contents of the resuspended cells and culture media into the T-225 flask containing the 45 ml of media.

Cap the T-225 flask.

Observe for presence of intact cells under the microscope. Place the T-225 flask immediately into a CO2 incubator and allow the cells to incubate overnight.

Expansion of Hybridoma Cell Line

Continue to monitor the cell culture for viability, concentration, and presence of contamination.

Monitor and adjust the cell suspension from the initial T-225 flask until the concentration is approximately 600,000 cells/ml to 800,000 cells/ml and a total of 200 to 250 ml of media.

Dislodge cells and add additional media as needed to meet minimum cell density requirements. Divide and transfer cell suspension into one new sterile T-225 flask. Place the 2×T-225 flasks into the CO2 incubator.

Monitor the cells from the 2×T-225 flasks until the concentration is approximately 600,000 cells/ml to 800,000 cells/ml, and a total of between 200 to 250 ml of media for each flask.

Dislodge cells and add additional media as needed to meet minimum cell density requirements. Divide and transfer the cell suspensions into 2 additional new sterile T-225 flasks for a total of 4×T-225 flasks. Return all flasks to the CO2 incubator.

Monitor the cells, and adjust volume in the 4×T-225 flasks until the cell concentration is approximately 600,000 cells/ml to 800,000 cells/ml with a total volume of approximately 250 ml per T-225 flask (or approximately 1000 ml total).

Continue to monitor the cells from the 4×T-225 flasks until the cells have grown to exhaustion, with a final viability of 0%-15%. The cell culture supernatant is now ready for the Clarification Process.

Clarification of Supernatant

Turn on the tabletop centrifuge. Place the 500 ml tube adapters into the rotor buckets, close the lid and set the temperature to 4° C. (+/−) 4° C.

Using aseptic technique, pour the media from all four of the now exhausted T-225 flasks into 2×500 ml conical centrifuge tubes.

Make sure the 2×500 ml tubes are balanced. Transfer supernatant from one tube to the other as necessary to balance them.

Centrifuge the exhausted supernatant at 1350 g (+/−40 g) for 15 minutes at 2° C. to 10° C.

After centrifugation is complete, aseptically decant the supernatant into a sterile 1000 ml storage bottle and secure with a sterile cap.

Aseptically transfer 1 ml to the microfuge tube. Store microfuge tube with sample at 2° C. to 10° C. (Protect from light).

The clarified supernatant sample is ready for IgG evaluation using the Easy-Titer® Assay.

Buffer Preparation

Binding Buffer:

Add approximately 600 ml of DI $H_2O$ to a clean beaker.

Add 77.28 ml of Boric Acid solution (4% W/V). Stir at room temperature with a clean stir bar.

Weigh out 233.76 g of Sodium Chloride and place into the solution while continuing to stir.

Bring solution up to approximately 950 ml with DI $H_2O$ and continue to stir.

When the Sodium Chloride has dissolved and the solution is clear, adjust the pH to 9.0±0.2 with Sodium Hydroxide.

Remove the solution to a clean 1000 ml graduated cylinder and QS to 1000 ml with DI $H_2O$.

Transfer the completed buffer to an appropriate storage bottle. This buffer may be stored for up to 7 days before use.

Repeat this entire process to prepare an additional 0.2 liters to 1.0 liter of Binding Buffer.

Elution Buffer

Weigh out 1.725 g of sodium phosphate, monobasic and place into a clean 250 ml beaker with a clean stir bar.

Weigh out 3.676 g of sodium citrate and place into the same clean 250 ml beaker.

Add approximately 175 ml of DI $H_2O$ and stir at room temperature until dissolved.

Weigh out 4.38 g of Sodium Chloride and place into the solution while continuing to stir.

Bring solution up to approximately 225 ml with DI $H_2O$ and continue to stir.

When the Sodium Chloride has dissolved and the solution is clear, adjust the pH to 3.5±0.2 with Hydrochloric Acid.

Remove the solution to a clean 250 ml graduated cylinder and QS to 250 ml with DI $H_2O$.

Connect a 500 ml sterile acetate vacuum filter unit (0.2 μm) to a vacuum pump system and filter sterilize the solution.

Remove the filter and close the container with a sterile cap.

Antibody Adsorption

Pour the Clarified Supernatant (~1 L) into a clean 4000 ml plastic beaker with a clean stir bar.

Add an approximately equal amount (~1 L) of the Binding Buffer to the clean 4000 ml plastic beaker containing the clarified supernatant. Add a clean stir bar.

Cover the beaker with clean plastic wrap and label "Antibody Binding."

Calculate the approximate amount of STREAMLINE® Protein A that will be needed using the data in Table 1.

TABLE 1

| Volume of Protein A Resin Required | |
| --- | --- |
| Quantity IgG (μg/ml) in Supernatant | Volume of Protein A Resin Required in Milliliters (ml) |
| >180-≦200 | 12.0 |
| >160-≦180 | 11.0 |
| >140-≦160 | 10.0 |
| >120-≦140 | 9.0 |

TABLE 1-continued

Volume of Protein A Resin Required

| Quantity IgG (µg/ml) in Supernatant | Volume of Protein A Resin Required in Milliliters (ml) |
|---|---|
| >100-≦120 | 8.0 |
| >80-≦100 | 7.0 |
| >60-≦80 | 6.0 |
| >40-≦60 | 4.5 |
| >20-≦40 | 3.5 |
| ≦20 | 2.0 |

Secure a clean Disposable Column and stopcock assembly to a ring stand and clamp. Close the stopcock.

Mix appropriate amount of STREAMLINE® Protein A beads by inverting the bottle several times. Withdraw the required volume and place into the Disposable Column.

Wash the STREAMLINE® Protein A beads with 10 ml of DI $H_2O$. Open the stopcock and allow the DI $H_2O$ to drain. Close the stopcock. Repeat with an additional 10 ml of DI $H_2O$.

Wash the STREAMLINE® Protein A beads with 10 ml of Binding Buffer. Open the stopcock and allow the Binding Buffer to drain. Close the stopcock. Repeat with an additional 10 ml of Binding Buffer.

Resuspend the STREAMLINE® Protein A beads in ~10 ml of the Clarified Supernatant and Binding Buffer solution (from the 4000 ml beaker) and transfer the beads into the 4000 ml beaker containing the Clarified Supernatant and Binding Buffer solution. Repeat as required to transfer any remaining beads. When completed, discard the column and stopcock.

Allow the mixture to mix vigorously at 2° C. to 10° C. for approximately 18 hours.

When mixing is complete, turn off the stir plate and remove the "Antibody Binding" beaker with the buffered supernatant and bead suspension back to the lab bench area. Allow the STREAMLINE® Protein A beads to settle to the bottom of the beaker (approximately 5 minutes).

Secure a clean Disposable Column and stopcock assembly to a ring stand and clamp. Close the stopcock.

Label a clean, 250 ml bottle or suitable container "Column Wash-Post Binding."

Label a clean plastic beaker "Supernatant-Post Binding."

Decant the supernatant from the 4000 ml beaker into the clean, labeled, 2 liter plastic beaker, leaving the beads in the bottom of the 4000 ml beaker. Cover the 2000 ml beaker containing the "Supernatant-Post Binding" solution with clean plastic wrap and store at 2° C. to 10° C.

Add approximately 15 ml of Binding Buffer into the decanted 4000 ml "Antibody Binding" beaker. Resuspend the STREAMLINE® Protein A beads and transfer them to the column. Open the stopcock and allow the Binding Buffer to drain into the "Column Wash-Post binding" container. Close the stopcock when drained.

Transfer any remaining STREAMLINE® Protein A beads in the "Antibody Binding" beaker by adding additional Binding Buffer, mixing, and transferring to the column as in the preceding steps. Close the stopcock when drained.

Calculate the approximate amount of Binding Buffer needed to wash the STREAMLINE® Protein A beads in the column using the data in Table 2.

TABLE 2

Binding Buffer Volume for Column Wash

| Quantity IgG (µg/ml) in Supernatant | Volume of Binding Buffer Required in Milliliters (ml) |
|---|---|
| >180-≦200 | 5 column washes total with 15.0 ml each |
| >160-≦180 | 5 column washes total with 15.0 ml each |
| >140-≦160 | 5 column washes total with 12.5 ml each |
| >120-≦140 | 5 column washes total with 12.5 ml each |
| >100-≦120 | 5 column washes total with 12.5 ml each |
| >80-≦100 | 5 column washes total with 10.0 ml each |
| >60-≦80 | 5 column washes total with 10.0 ml each |
| >40-≦60 | 5 column washes total with 7.5 ml each |
| >20-≦40 | 5 column washes total with 5.0 ml each |
| ≦20 | 5 column washes total with 5.0 ml each |

Wash the STREAMLINE® Protein A beads in the column with the appropriate volume of Binding Buffer for the appropriate number of washes, continuing to collect the effluent into the "Column Wash-Post Binding" container.

When completed, close the stopcock. Store the "Column Wash-Post Binding" container at 2° C. to 10° C.

Determine the Total Volumes of Elution Buffer and Neutralization Buffer needed to elute the STREAMLINE® Protein A beads in the column from Table 3.

TABLE 3

Determination of Amount of Elution Buffer and Neutralization Buffer

| Quantity IgG (µg/ml) in Supernatant | Total Volume of Elution Buffer Required (ml) | Total Volume of Neutralization Buffer Required (ml) | Volume of Elution Buffer Required per fraction (ml) | Volume of Neutralization Buffer Required per fraction (ml) |
|---|---|---|---|---|
| >180-≦200 | 72 | 7.2 | 12 | 1.2 |
| >160-≦180 | 66 | 6.6 | 11 | 1.1 |
| >140-≦160 | 60 | 6.0 | 10 | 1.0 |
| >120-≦140 | 54 | 5.4 | 9 | 0.9 |
| >100-≦120 | 48 | 4.8 | 8 | 0.8 |

TABLE 3-continued

Determination of Amount of Elution Buffer and Neutralization Buffer

| Quantity IgG (μg/ml) in Supernatant | Total Volume of Elution Buffer Required (ml) | Total Volume of Neutralization Buffer Required (ml) | Volume of Elution Buffer Required per fraction (ml) | Volume of Neutralization Buffer Required per fraction (ml) |
|---|---|---|---|---|
| >80-≦100 | 42 | 4.2 | 7 | 0.7 |
| >60-≦80 | 36 | 3.6 | 6 | 0.6 |
| >40-≦60 | 27 | 2.7 | 4.5 | 0.45 |
| >20-≦40 | 21 | 2.1 | 3.5 | 0.35 |
| ≦20 | 12 | 1.2 | 2 | 0.2 |

Label 9 sterile conical centrifuge tubes "Eluted Antibody", Fraction # (1 through 9).

Place the appropriate volume of Neutralization Buffer required per fraction (as determined from Table "C" above) into each of the 9 "Eluted Antibody" fraction tubes and place securely under the column stopcock outlet.

Elute the STREAMLINE® Protein A beads in the column fraction by fraction with the appropriate volume of Elution Buffer required per fraction (as determined from Table 3 above) while collecting the eluate into each of the "Eluted Antibody" tubes containing Neutralization Buffer.

When the elutions are complete, mix each "Eluted Antibody" fraction tube gently by swirling several times. Remove approximately 50 μl of fraction # 3 and place on a pH test paper strip to ensure that the eluate has been neutralized to an approximate pH between 6.5 to 8.5. If required, add additional Neutralizing Buffer or Elution Buffer as needed to bring pH into range.

When pH evaluation is completed, perform an Absorbance Scan of a sample from each fraction at 280 nm-400 nm to determine the approximate concentration of IgG in the eluate prior to proceeding to the Dialysis Process.

Accept fractions as part of the Eluate Pool if the A280-A400 value is ≧0.200.

Reject fractions as part of the Eluate Pool if the A280-A400 value is <0.200.

Label a sterile conical centrifuge tube "Eluted Antibody," "Eluate Pool," and combine all fractions that were Accepted as part of the pool.

Perform an Absorbance Scan of a sample of the Eluate Pool to determine the approximate concentration of IgG in the eluate prior to proceeding to the Dialysis Process.

Estimate the volume of the Eluate Pool and calculate the approximate total mgs of IgG.

Volume of Eluate Pool:_____mls×_____IgG mg/ml=_____Total mgs of IgG

Antibody Dialysis

Remove the "Eluted Antibody" tube from 2° C. to 10° C.

Calculate the approximate length of Dialysis Tubing that will be needed to dialyze the antibody eluate using the approximate volume of eluate and the data in Table 4.

TABLE 4

Calculation of Length of Dialysis Tubing Needed

| Approximate Volume of Eluent (ml) | Volume/length Ratio of Dialysis Tubing | Approximate Length Needed for Eluent Sample (cm) | Head Space of 20% (cm) | Approximate Length Needed for Sample plus Headspace (cm) | Approximate Length Needed for Tie Off of Tubing (cm) | Approximate Total Length of Dialysis Tubing Needed (cm) |
|---|---|---|---|---|---|---|
| 39.6 | 2 | 20 | 4 | 24 | 15 | 63 |
| 36.3 | 2 | 18 | 4 | 22 | 15 | 59 |
| 33.0 | 2 | 17 | 3 | 20 | 15 | 55 |
| 29.7 | 2 | 15 | 3 | 18 | 15 | 51 |
| 26.4 | 2 | 13 | 3 | 16 | 15 | 47 |
| 23.1 | 2 | 12 | 2 | 14 | 15 | 43 |
| 19.8 | 2 | 10 | 2 | 12 | 15 | 39 |
| 14.85 | 2 | 7 | 1 | 9 | 15 | 33 |
| 11.55 | 2 | 6 | 1 | 7 | 15 | 29 |
| 6.6 | 2 | 3 | 1 | 4 | 15 | 23 |

Cut the appropriate length of dialysis tubing required. (Spectra/Por® 2 Regenerated Cellulose Membrane, 12,000-14,000 Dalton Molecular Weight Cutoff (MWCO), 16 mm Diameter, Spectrum Laboratories Inc., Cat. No. 132678)

Hydrate the dialysis membrane tubing in 1000 ml of $DIH_2O$ for >30 minutes.

Calculate the approximate volume of Dialysis Buffer needed to dialyze the antibody eluate using the data in Table 5.

TABLE 5

Volume of Dialysis Buffer Required

| Quantity IgG (µg/ml) in Supernatant | Final Volume of Eluted Antibody in Milliliters (ml) | Length of Dialysis Tubing Needed (cm) | Volume of Dialysis Buffer (1 × PBS) Needed in Liters |
|---|---|---|---|
| >180-≦200 | 39.6 ml | 63 cm | 3 complete changes of 4.0 Liters |
| >160-≦180 | 36.3 ml | 59 cm | 3 complete changes of 3.6 Liters |
| >140-≦160 | 33.0 ml | 55 cm | 3 complete changes of 3.3 Liters |
| >120-≦140 | 29.7 ml | 51 cm | 3 complete changes of 3.0 Liters |
| >100-≦120 | 26.4 ml | 47 cm | 3 complete changes of 2.6 Liters |
| >80-≦100 | 23.1 ml | 43 cm | 3 complete changes of 2.3 Liters |
| >60-≦80 | 19.8 ml | 39 cm | 3 complete changes of 1.9 Liters |
| >40-≦60 | 14.85 ml | 33 cm | 3 complete changes of 1.5 Liters |
| >20-≦40 | 11.55 ml | 29 cm | 3 complete changes of 1.2 Liters |
| ≦20 | 6.6 ml | 23 cm | 3 complete changes of 0.7 Liters |

Place the appropriate amount of Dialysis Buffer into a suitable sized plastic beaker. Label the beaker "Dialyzed Antibody." Add a clean stir bar and place the beaker on a stir plate inside a refrigerator or cold room at 2° C. to 10° C.

Rinse the dialysis tubing thoroughly in $DI-H_2O$. Tie two end knots approximately 7 cm from one end of the dialysis tubing and secure tightly.

Add approximately 5 ml of $DI-H_2O$ into the dialysis tubing.

Fill the dialysis tubing with the eluted antibody from the "Eluted Antibody" collection tube.

Tie two end knots approximately 7 cm from the remaining open end of the dialysis tubing and secure tightly. Ensure that the headspace is approximately that as derived from Table 4.

Place the filled and closed dialysis tubing into the dialysis reservoir with the appropriate volume of 1×PBS (from Table 5).

Cover the beaker with clean plastic wrap. Adjust the speed on the stir plate such that the dialysis sample spins freely, but is not pulled down into the vortex of the dialysate. Dialysis should take place at 2° C. to 10° C. with 3 buffer exchanges in total within a 24 hour period.

Antibody Filtration

Label a sterile collection tube "Dialyzed Antibody."

Remove the dialyzed sample tubing from the dialysis beaker. Cut the dialysis tubing open at one end and transfer the dialyzed sample into the "Dialyzed Antibody" centrifuge tube.

Label another sterile collection tube "Dialyzed Antibody."

Select a sterile Luer Lok syringe with adequate capacity to hold the final dialyszed volume.

Attach an ACRODISC® Syringe Filter to the opening of the syringe (0.2 µm HT TUFFRYN® Membrane, Low Protein binding, Gelman Laboratories, Cat. No. 4192). Remove the plunger from the syringe and while holding the syringe upright, transfer the dialyszed monoclonal antibody from the "Dialyzed Antibody" tube into the syringe. Replace the plunger.

Hold the ACRODISC® Syringe Filter over the opened, sterile, labeled "Purified Antibody" collection tube, and depress the syringe plunger to filter the purified antibody into the "Purified Antibody" tube.

When filtration is complete, cap the "Purified Antibody" tube and store at 2° C. to 10° C.

Determine concentration of purified monoclonal antibody using A280 procedure.

Example 3

General Method for Epitope Mapping

General Approach

Epitope mapping is performed to identify the linear amino acid sequence within an antigenic protein (i.e., the epitope) that is recognized by a particular monoclonal antibody. A general approach for epitope mapping requires the expression of the full-length protein, as well as various fragments (i.e., truncated forms) of the protein, generally in a heterologous expression system. These various recombinant proteins are then used to determine if the specific monoclonal antibody is capable of binding one or more of the truncated forms of the target protein. Through the use of reiterative truncation and the generation of recombinant proteins with overlapping amino acid regions, it is possible to identify the region that is recognized by the monoclonal antibody under investigation. Western blot analysis or ELISA is employed to determine if the specific monoclonal antibody under investigation is capable of binding one or more of the recombinant protein fragments. This approach can ultimately identify the peptide regions that contains the epitope and, in some cases, to refine the epitope precisely to an 8-11 amino acid sequence.

Construct Design and Creation

The first step in epitope mapping is the design of nested gene truncations. Frequently, the gene is divided into four equal parts for further analysis.

Gene Cloning Strategy

The general cloning strategy begins with PCR-based generation of the cloned gene fragments. In order to efficiently express the cloned fragment, especially when using small amino acid regions, the cloned fragment is expressed as a fusion protein, i.e. fused to another carrier protein that is stably expressed in the system. Green fluorescent protein (GFP) is frequently used as the carrier protein. GFP is included as a fusion partner to stabilize the truncation fragments and improve expression during the subsequent in vitro protein expression step. GFP also permits the tracking of fusion-protein expression using anti-GFP antibodies.

Cloning to create the GFP-protein construct is performed using either the mega-priming approach or through the use of plasmid cloning into the pScreen-GFP vector. Generally, the truncation fragments are fused to GFP and control sequences necessary for protein expression using a technique called megapriming.

Megapriming is the joining of two or more DNA fragments by annealing homologous regions at the end of the respective fragments and extending the annealed single-stranded DNA with a thermostable DNA polymerase. This process creates one large DNA fragment from two or more smaller fragments, linking them by their shared sequence. This large fragment is then amplified using standard PCR.

If megapriming cannot be used successfully, the truncation fragments can be cloned into a plasmid containing GFP and protein-expression control sequences. This cloning creates the GFP/fragment fusions necessary for epitope mapping. The remainder of the protocol can then proceed as described below.

Protein Expression

The expression constructs created by, for example, megapriming are then introduced into the Rapid Translation System (RTS). RTS is a cell-free protein expression system derived from *E. coli* lysates. This system permits rapid (3-4 hour) expression of proteins from DNA templates.

If RTS does not produce adequate levels of protein expression, then the truncation fragments will be cloned into the GFP protein-expression plasmid. These fusion plasmids are then transformed into an *E. coli* strain optimized for protein expression. Protein expression is induced in a growing culture of bacteria and, following outgrowth, the cells are lysed. The proteins in the complex cell lysate are then separated by polyacrylamide gel electrophoresis (PAGE), and the remainder of the protocol is the same as below.

Protein Detection and Epitope Mapping

Protein fragments produced by RTS are separated using PAGE and transferred onto nitrocellulose membranes. The membrane-bound proteins are then exposed to the antibody under investigation in solution. Antibody/protein binding is identified using colorimetric techniques known in the art.

Antibody binding of the full-length protein and some subset of the truncated protein fragments constitutes a positive result. If the absence of a particular section of the protein eliminates antibody binding, then the epitope lies on this fragment.

If the antibody to be mapped does not recognize protein bound to nitrocellulose membranes, then alternative methods for detecting antibody/protein interactions, such as, for example, ELISA or immunoprecipitation are used. Methods for detecting antibody/protein interactions are well known in the art.

Refining the Epitope Location

Since the above-described protocol will only narrow the location of the epitope down to approximately one-quarter of the protein, it is necessary to repeat the process on the quarter of the protein determined to contain the epitope in order to further resolve the location of the epitope. For a very large protein, it may be necessary to repeat this process two to three times to narrow the epitope down to 8-15 amino acids.

Example 4

Characterization of Epitopes for MCM2 Monoclonal Antibodies 27C5.6 and 26H6.19

Epitope mapping for MCM2 Monoclonal Antibodies 27C5.6 and 26H6.19 was carried out essentially as described in Example 3. Specifically, PCR was used to create MCM2 gene truncations, followed by RTS to generate recombinant MCM2 protein fragments, and finally western blotting to detect antibody binding to MCM2. GFP was joined with the MCM2 gene truncations in a second round of PCR to ensure robust and stable expression in RTS.

The full-length coding sequence for MCM2 (SEQ ID NO:2; NM_004526) has a size of 2715 bp. However, the cDNA that was used to express the recombinant MCM2 protein and that was used to immunize mice during the production of MCM2 antibodies had a gene size of 2688 bp (SEQ ID NO:5). The truncated MCM2 cDNA used had a 27 bp region missing at the 5' end of the MCM2 protein, specifically the fragment ATGGCGGAATCATCGGAATCCTTCACC (SEQ ID NO:6). The following sequential steps were carried out in order to epitope map the MCM2-27C5.6 antibody:

Since the MCM2 gene was large (>1000 bp) and to minimize the number of iterations of PCR needed, the gene was equally divided into six regions [1-6] of approximately 400 bp. Overlapping sequences, which contain homologous sequence to permit mega priming during a second PCR cycle and restriction sites for a second option of sub-cloning into pScreen-GFP plasmid, were added to the gene of interest during the first PCR. The first round of PCR created fragments of the truncated MCM2 nucleotide sequence (SEQ ID NO:5) including: region [1] was 1-426 bp, region [1-2] was 1-888 bp, region [1-3] was 1-1377 bp, region [1-4] was 1-1845 bp, region [1-5] was 1-2241 bp, region [1-6] was 1-2688 bp, and finally region [2-6] was 427-2688 bp. Individual regions (example region [5]) were not expressed to avoid missing epitopes that were present in junction sequence between regions.

The first round PCR products of MCM2 were subcloned into pSCREEN-GFP (BamH1-Xho1), as the fragment sizes were too large for mega-priming. The only truncation that was unsuccessful was the full length region [1-6]. The original primers used to amplify the full-length gene and truncations were engineered to include restriction sites (5' end BAMH1; 3'end XHO1) to allow direct subcloning into pSCREEN-GFP.

The GFP-gene fusions created were used as a template for protein production in the RTS reaction using the RTS 100 *E. coli* HY kit from Roche. The protein products from RTS were acetone precipitated, loaded directly onto a denaturing polyacrylimide gel, and analyzed by western blotting. The western blot was probed directly with the 27C5.6 monoclonal antibody and GFP antibodies.

The first round of RTS products were probed with both GFP antibodies and the MCM2 monoclonal antibody 27C5.6. A positive band was detected in region [1-3]. The above process was repeated using the fragment encompassed by region [1-3] as the starting sequence.

A second round of RTS produced a positive result for the 27C5.6 antibody in the region MCM2-3Q3 (CQSAGPFEVNMEETIYQNYQRIRIQESP (SEQ ID NO:7); corresponding to amino acid residues 355 to 382 of SEQ ID NO:1). The above process was repeated using the fragment encompassed by region MCM2-3Q3 as the starting sequence.

A third round of RTS produced a positive result for the 27C5.6 antibody in the region MCM2-3Q3.2 (IYQNYQRIRIQESP (SEQ ID NO:3); corresponding to amino acid residues 369 to 382 of SEQ ID NO:1). No positive result was obtained in region MCM2-3Q3.1 (CQSAGPFEVNMEET (SEQ ID NO:8); corresponding to amino acid residues 355 to 368 of SEQ ID NO:1) or in MCM2-3Q3.2 (EVNMEETIYQNYQR (SEQ ID NO:9); corresponding to amino acid residues 362 to 375 of SEQ ID NO:1).

Results

Initial results showed that the epitope for the MCM2 monoclonal antibody 27C5.6 is located within the N-terminal region of the MCM2 protein. Continued truncations of the MCM2 protein showed that the epitope recognized by 27C5.6 is located within a fourteen amino acid region, specifically corresponding to amino acid residues 369-382 of SEQ ID NO:1 (IYQNYQRIRIQESP (SEQ ID NO:3)). Additional rounds of RTS may be able to refine the epitope location further.

The identical process described above was used to identify the epitope for MCM2 monoclonal antibody 26H6.19. Initial results indicated that the epitope was located within the C-terminal region of the MCM2 protein. The epitope was preliminarily defined to a twenty-three amino acid region, specifically corresponding to amino acid residues 688-710 of SEQ ID NO:1 (PSNKEEEGLANGSAAEPAMPNTY (SEQ ID NO:4)). Further analysis refined the epitope of MCM2 monoclonal antibody 26H6.19 to a ten amino acid region comprising amino acid residues 683-692 of SEQ ID NO:1 (HVRHHPSNKE (SEQ ID NO:14)).

---

That which is claimed:

1. A monoclonal antibody that is capable of specifically binding to MCM2, wherein the antibody is selected from the group consisting of:
   (a) the monoclonal antibody produced by the hybridoma cell line 27C5.6, deposited with the ATCC as Patent Deposit No. PTA-6668;
   (b) the monoclonal antibody produced by the hybridoma cell line 26H6.19, deposited with the ATCC as Patent Deposit No. PTA-6667;
   (c) a monoclonal antibody that binds to the amino acid sequence set forth in SEQ ID NO:3;
   (d) a monoclonal antibody that binds to the amino acid sequence of SEQ ID NO:14; and
   (e) an antigen binding fragment of a monoclonal antibody of (a)-(d), wherein the fragment retains the capability of specifically binding to MCM2.

2. The hybridoma cell line 27C5.6, deposited with the ATCC as Patent Deposit No. PTA-6668.

3. The hybridoma cell line 26H6.19, deposited with the ATCC as Patent Deposit No. PTA-6667.

4. A hybridoma cell line capable of producing a monoclonal antibody of claim 1.

5. A kit for diagnosing high-grade cervical disease comprising at least one monoclonal antibody according to claim 1.

6. The kit of claim 5, wherein the monoclonal antibody is the monoclonal antibody produced by the hybridoma cell line 27C5.6, deposited with the ATCC as Patent Deposit No. PTA-6668, or the monoclonal antibody produced by the hybridoma cell line 26H6.19, deposited with the ATCC as Patent Deposit No. PTA-6667.

7. The kit of claim 5 comprising at least two antibodies, wherein a first antibody is the monoclonal antibody produced by the hybridoma cell line 27C5.6, deposited with the ATCC as Patent Deposit No. PTA-6668, and a second antibody is the monoclonal antibody produced by the hybridoma cell line 26H6.19, deposited with the ATCC as Patent Deposit No. PTA-6667.

8. The kit of claim 7 further comprising an antibody that specifically binds to Topo2A.

9. The kit of claim 7, wherein each antibody is provided as a separate antibody reagent.

10. The kit of claim 7, wherein all of the antibodies are provided as an antibody cocktail.

11. The kit of claim 5 further comprising reagents for Pap staining.

12. The kit of claim 11, wherein the reagents for Pap staining comprise EA50 and Orange G.

13. The monoclonal antibody of claim 1, wherein the monoclonal antibody is the monoclonal antibody produced by the hybridoma cell line 27C5.6, deposited with the ATCC as Patent Deposit No. PTA-6668.

14. The monoclonal antibody of claim 1, wherein the monoclonal antibody is the monoclonal antibody produced by the hybridoma cell line 27C5.6, deposited with the ATCC as Patent Deposit No. PTA-6667.

* * * * *

SEQUENCE LISTING

<160> NUMBER OF SEQ ID NOS: 14

<210> SEQ ID NO 1
<211> LENGTH: 904
<212> TYPE: PRT
<213> ORGANISM: Homo sapiens

<400> SEQUENCE: 1

```
Met Ala Glu Ser Ser Glu Ser Phe Thr Met Ala Ser Ser Pro Ala Gln
 1               5                  10                  15

Arg Arg Arg Gly Asn Asp Pro Leu Thr Ser Ser Pro Gly Arg Ser Ser
            20                  25                  30

Arg Arg Thr Asp Ala Leu Thr Ser Ser Pro Gly Arg Asp Leu Pro Pro
        35                  40                  45

Phe Glu Asp Glu Ser Glu Gly Leu Leu Gly Thr Glu Gly Pro Leu Glu
    50                  55                  60

Glu Glu Glu Asp Gly Glu Glu Leu Ile Gly Asp Gly Met Glu Arg Asp
65                  70                  75                  80

Tyr Arg Ala Ile Pro Glu Leu Asp Ala Tyr Glu Ala Glu Gly Leu Ala
                85                  90                  95

Leu Asp Asp Glu Asp Val Glu Glu Leu Thr Ala Ser Gln Arg Glu Ala
            100                 105                 110

Ala Glu Arg Ala Met Arg Gln Arg Asp Arg Glu Ala Gly Arg Gly Leu
        115                 120                 125

Gly Arg Met Arg Arg Gly Leu Leu Tyr Asp Ser Asp Glu Glu Asp Glu
    130                 135                 140

Glu Arg Pro Ala Arg Lys Arg Arg Gln Val Glu Arg Ala Thr Glu Asp
145                 150                 155                 160

Gly Glu Glu Asp Glu Glu Met Ile Glu Ser Ile Glu Asn Leu Glu Asp
                165                 170                 175

Leu Lys Gly His Ser Val Arg Glu Trp Val Ser Met Ala Gly Pro Arg
            180                 185                 190

Leu Glu Ile His His Arg Phe Lys Asn Phe Leu Arg Thr His Val Asp
        195                 200                 205

Ser His Gly His Asn Val Phe Lys Glu Arg Ile Ser Asp Met Cys Lys
    210                 215                 220

Glu Asn Arg Glu Ser Leu Val Val Asn Tyr Glu Asp Leu Ala Ala Arg
225                 230                 235                 240

Glu His Val Leu Ala Tyr Phe Leu Pro Glu Ala Pro Ala Glu Leu Leu
                245                 250                 255

Gln Ile Phe Asp Glu Ala Ala Leu Glu Val Val Leu Ala Met Tyr Pro
            260                 265                 270

Lys Tyr Asp Arg Ile Thr Asn His Ile His Val Arg Ile Ser His Leu
        275                 280                 285

Pro Leu Val Glu Glu Leu Arg Ser Leu Arg Gln Leu His Leu Asn Gln
```

```
                    290                 295                 300
Leu Ile Arg Thr Ser Gly Val Val Thr Ser Cys Thr Gly Val Leu Pro
305                 310                 315                 320

Gln Leu Ser Met Val Lys Tyr Asn Cys Asn Lys Cys Asn Phe Val Leu
                325                 330                 335

Gly Pro Phe Cys Gln Ser Gln Asn Gln Glu Val Lys Pro Gly Ser Cys
                340                 345                 350

Pro Glu Cys Gln Ser Ala Gly Pro Phe Glu Val Asn Met Glu Glu Thr
            355                 360                 365

Ile Tyr Gln Asn Tyr Gln Arg Ile Arg Ile Gln Glu Ser Pro Gly Lys
        370                 375                 380

Val Ala Ala Gly Arg Leu Pro Arg Ser Lys Asp Ala Ile Leu Leu Ala
385                 390                 395                 400

Asp Leu Val Asp Ser Cys Lys Pro Gly Asp Glu Ile Glu Leu Thr Gly
                405                 410                 415

Ile Tyr His Asn Asn Tyr Asp Gly Ser Leu Asn Thr Ala Asn Gly Phe
                420                 425                 430

Pro Val Phe Ala Thr Val Ile Leu Ala Asn His Val Ala Lys Lys Asp
            435                 440                 445

Asn Lys Val Ala Val Gly Glu Leu Thr Asp Glu Asp Val Lys Met Ile
        450                 455                 460

Thr Ser Leu Ser Lys Asp Gln Gln Ile Gly Glu Lys Ile Phe Ala Ser
465                 470                 475                 480

Ile Ala Pro Ser Ile Tyr Gly His Glu Asp Ile Lys Arg Gly Leu Ala
                485                 490                 495

Leu Ala Leu Phe Gly Gly Glu Pro Lys Asn Pro Gly Gly Lys His Lys
                500                 505                 510

Val Arg Gly Asp Ile Asn Val Leu Leu Cys Gly Asp Pro Gly Thr Ala
            515                 520                 525

Lys Ser Gln Phe Leu Lys Tyr Ile Glu Lys Val Ser Ser Arg Ala Ile
        530                 535                 540

Phe Thr Thr Gly Gln Gly Ala Ser Ala Val Gly Leu Thr Ala Tyr Val
545                 550                 555                 560

Gln Arg His Pro Val Ser Arg Glu Trp Thr Leu Glu Ala Gly Ala Leu
                565                 570                 575

Val Leu Ala Asp Arg Gly Val Cys Leu Ile Asp Glu Phe Asp Lys Met
                580                 585                 590

Asn Asp Gln Asp Arg Thr Ser Ile His Glu Ala Met Glu Gln Gln Ser
            595                 600                 605

Ile Ser Ile Ser Lys Ala Gly Ile Val Thr Ser Leu Gln Ala Arg Cys
        610                 615                 620

Thr Val Ile Ala Ala Asn Pro Ile Gly Gly Arg Tyr Asp Pro Ser
625                 630                 635                 640

Leu Thr Phe Ser Glu Asn Val Asp Leu Thr Glu Pro Ile Ile Ser Arg
                645                 650                 655

Phe Asp Ile Leu Cys Val Val Arg Asp Thr Val Asp Pro Val Gln Asp
                660                 665                 670

Glu Met Leu Ala Arg Phe Val Val Gly Ser His Val Arg His His Pro
            675                 680                 685

Ser Asn Lys Glu Glu Glu Gly Leu Ala Asn Gly Ser Ala Ala Glu Pro
        690                 695                 700

Ala Met Pro Asn Thr Tyr Gly Val Glu Pro Leu Pro Gln Glu Val Leu
705                 710                 715                 720
```

```
Lys Lys Tyr Ile Ile Tyr Ala Lys Glu Arg Val His Pro Lys Leu Asn
            725                 730                 735

Gln Met Asp Gln Asp Lys Val Ala Lys Met Tyr Ser Asp Leu Arg Lys
        740                 745                 750

Glu Ser Met Ala Thr Gly Ser Ile Pro Ile Thr Val Arg His Ile Glu
    755                 760                 765

Ser Met Ile Arg Met Ala Glu Ala His Ala Arg Ile His Leu Arg Asp
770                 775                 780

Tyr Val Ile Glu Asp Asp Val Asn Met Ala Ile Arg Val Met Leu Glu
785                 790                 795                 800

Ser Phe Ile Asp Thr Gln Lys Phe Ser Val Met Arg Ser Met Arg Lys
                805                 810                 815

Thr Phe Ala Arg Tyr Leu Ser Phe Arg Asp Asn Asn Glu Leu Leu
            820                 825                 830

Leu Phe Ile Leu Lys Gln Leu Val Ala Glu Gln Val Thr Tyr Gln Arg
        835                 840                 845

Asn Arg Phe Gly Ala Gln Gln Asp Thr Ile Glu Val Pro Glu Lys Asp
    850                 855                 860

Leu Val Asp Lys Ala Arg Gln Ile Asn Ile His Asn Leu Ser Ala Phe
865                 870                 875                 880

Tyr Asp Ser Glu Leu Phe Arg Met Asn Lys Phe Ser His Asp Leu Lys
                885                 890                 895

Arg Lys Met Ile Leu Gln Gln Phe
            900

<210> SEQ ID NO 2
<211> LENGTH: 3453
<212> TYPE: DNA
<213> ORGANISM: Homo sapiens
<220> FEATURE:
<221> NAME/KEY: CDS
<222> LOCATION: (58)...(2772)

<400> SEQUENCE: 2
acttttcgcg cgaaacctgg ttgttgctgt agtggcggag aggatcgtgg tactgct atg     60
                                                                Met
                                                                 1 gcg gaa tca tcg gaa tcc ttc acc atg gca tcc agc ccg gcc cag cgt      108
Ala Glu Ser Ser Glu Ser Phe Thr Met Ala Ser Ser Pro Ala Gln Arg
        5                  10                  15 cgg cga ggc aat gat cct ctc acc tcc agc cct ggc cga agc tcc cgg      156
Arg Arg Gly Asn Asp Pro Leu Thr Ser Ser Pro Gly Arg Ser Ser Arg
    20                  25                  30 cgt act gat gcc ctc acc tcc agc cct ggc cgt gac ctt cca cca ttt      204
Arg Thr Asp Ala Leu Thr Ser Ser Pro Gly Arg Asp Leu Pro Pro Phe
35                  40                  45 gag gat gag tcc gag ggg ctc cta gga aca gag ggg ccc ctg gag gaa      252
Glu Asp Glu Ser Glu Gly Leu Leu Gly Thr Glu Gly Pro Leu Glu Glu
 50                  55                  60                  65 gaa gag gat gga gag gag ctc att gga gat ggc atg gaa agg gac tac      300
Glu Glu Asp Gly Glu Glu Leu Ile Gly Asp Gly Met Glu Arg Asp Tyr
                 70                  75                  80 cgc gcc atc cca gag ctg gac gcc tat gag gcc gag gga ctg gct ctg      348
Arg Ala Ile Pro Glu Leu Asp Ala Tyr Glu Ala Glu Gly Leu Ala Leu
             85                  90                  95 gat gat gag gac gta gag gag ctg acg gcc agt cag agg gag gca gca      396
Asp Asp Glu Asp Val Glu Glu Leu Thr Ala Ser Gln Arg Glu Ala Ala
        100                 105                 110
```

-continued

| | |
|---|---|
| gag cgg gcc atg cgg cag cgt gac cgg gag gct ggc cgg ggc ctg ggc<br>Glu Arg Ala Met Arg Gln Arg Asp Arg Glu Ala Gly Arg Gly Leu Gly<br>115                        120                       125 | 444 |
| cgc atg cgc cgt ggg ctc ctg tat gac agc gat gag gag gac gag gag<br>Arg Met Arg Arg Gly Leu Leu Tyr Asp Ser Asp Glu Glu Asp Glu Glu<br>130                        135                       140                    145 | 492 |
| cgc cct gcc cgc aag cgc cgc cag gtg gag cgg gcc acg gag gac ggc<br>Arg Pro Ala Arg Lys Arg Arg Gln Val Glu Arg Ala Thr Glu Asp Gly<br>                      150                       155                       160 | 540 |
| gag gag gac gag gag atg atc gag agc atc gag aac ctg gag gat ctc<br>Glu Glu Asp Glu Glu Met Ile Glu Ser Ile Glu Asn Leu Glu Asp Leu<br>                165                       170                       175 | 588 |
| aaa ggc cac tct gtg cgc gag tgg gtg agc atg gcg ggc ccc cgg ctg<br>Lys Gly His Ser Val Arg Glu Trp Val Ser Met Ala Gly Pro Arg Leu<br>180                        185                       190 | 636 |
| gag atc cac cac cgc ttc aag aac ttc ctg cgc act cac gtc gac agc<br>Glu Ile His His Arg Phe Lys Asn Phe Leu Arg Thr His Val Asp Ser<br>195                        200                       205 | 684 |
| cac ggc cac aac gtc ttc aag gag cgc atc agc gac atg tgc aaa gag<br>His Gly His Asn Val Phe Lys Glu Arg Ile Ser Asp Met Cys Lys Glu<br>210                        215                       220                    225 | 732 |
| aac cgt gag agc ctg gtg gtg aac tat gag gac ttg gca gcc agg gag<br>Asn Arg Glu Ser Leu Val Val Asn Tyr Glu Asp Leu Ala Ala Arg Glu<br>                      230                       235                    240 | 780 |
| cac gtg ctg gcc tac ttc ctg cct gag gca ccg gcg gag ctg ctg cag<br>His Val Leu Ala Tyr Phe Leu Pro Glu Ala Pro Ala Glu Leu Leu Gln<br>                      245                       250                   255 | 828 |
| atc ttt gat gag gct gcc ctg gag gtg gta ctg gcc atg tac ccc aag<br>Ile Phe Asp Glu Ala Ala Leu Glu Val Val Leu Ala Met Tyr Pro Lys<br>                260                       265                    270 | 876 |
| tac gac cgc atc acc aac cac atc cat gtc cgc atc tcc cac ctg cct<br>Tyr Asp Arg Ile Thr Asn His Ile His Val Arg Ile Ser His Leu Pro<br>275                        280                       285 | 924 |
| ctg gtg gag gag ctg cgc tcg ctg agg cag ctg cat ctg aac cag ctg<br>Leu Val Glu Glu Leu Arg Ser Leu Arg Gln Leu His Leu Asn Gln Leu<br>290                        295                       300                   305 | 972 |
| atc cgc acc agt ggg gtg gtg acc agc tgc act ggc gtc ctg ccc cag<br>Ile Arg Thr Ser Gly Val Val Thr Ser Cys Thr Gly Val Leu Pro Gln<br>                      310                       315                    320 | 1020 |
| ctc agc atg gtc aag tac aac tgc aac aag tgc aat ttc gtc ctg ggt<br>Leu Ser Met Val Lys Tyr Asn Cys Asn Lys Cys Asn Phe Val Leu Gly<br>                      325                       330                    335 | 1068 |
| cct ttc tgc cag tcc cag aac cag gag gtg aaa cca ggc tcc tgt cct<br>Pro Phe Cys Gln Ser Gln Asn Gln Glu Val Lys Pro Gly Ser Cys Pro<br>                      340                       345                    350 | 1116 |
| gag tgc cag tcg gcc ggc ccc ttt gag gtc aac atg gag gag acc atc<br>Glu Cys Gln Ser Ala Gly Pro Phe Glu Val Asn Met Glu Glu Thr Ile<br>355                        360                       365 | 1164 |
| tat cag aac tac cag cgt atc cga atc cag gag agt cca ggc aaa gtg<br>Tyr Gln Asn Tyr Gln Arg Ile Arg Ile Gln Glu Ser Pro Gly Lys Val<br>370                        375                       380                   385 | 1212 |
| gcg gct ggc cgg ctg ccc cgc tcc aag gac gcc att ctc ctc gca gat<br>Ala Ala Gly Arg Leu Pro Arg Ser Lys Asp Ala Ile Leu Leu Ala Asp<br>                      390                       395                    400 | 1260 |
| ctg gtg gac agc tgc aag cca gga gac gag ata gag ctg act ggc atc<br>Leu Val Asp Ser Cys Lys Pro Gly Asp Glu Ile Glu Leu Thr Gly Ile<br>                      405                       410                   415 | 1308 |
| tat cac aac aac tat gat ggc tcc ctc aac act gcc aat ggc ttc cct<br>Tyr His Asn Asn Tyr Asp Gly Ser Leu Asn Thr Ala Asn Gly Phe Pro | 1356 |

-continued

```
            420                 425                 430
gtc ttt gcc act gtc atc cta gcc aac cac gtg gcc aag aag gac aac    1404
Val Phe Ala Thr Val Ile Leu Ala Asn His Val Ala Lys Lys Asp Asn
    435                 440                 445 aag gtt gct gta ggg gaa ctg acc gat gaa gat gtg aag atg atc act    1452
Lys Val Ala Val Gly Glu Leu Thr Asp Glu Asp Val Lys Met Ile Thr
450                 455                 460                 465 agc ctc tcc aag gat cag cag atc gga gag aag atc ttt gcc agc att    1500
Ser Leu Ser Lys Asp Gln Gln Ile Gly Glu Lys Ile Phe Ala Ser Ile
            470                 475                 480 gct cct tcc atc tat ggt cat gaa gac atc aag aga ggc ctg gct ctg    1548
Ala Pro Ser Ile Tyr Gly His Glu Asp Ile Lys Arg Gly Leu Ala Leu
        485                 490                 495 gcc ctg ttc gga ggg gag ccc aaa aac cca ggt ggc aag cac aag gta    1596
Ala Leu Phe Gly Gly Glu Pro Lys Asn Pro Gly Gly Lys His Lys Val
    500                 505                 510 cgt ggt gat atc aac gtg ctc ttg tgc gga gac cct ggc aca gcg aag    1644
Arg Gly Asp Ile Asn Val Leu Leu Cys Gly Asp Pro Gly Thr Ala Lys
515                 520                 525 tcg cag ttt ctc aag tat att gag aaa gtg tcc agc cga gcc atc ttc    1692
Ser Gln Phe Leu Lys Tyr Ile Glu Lys Val Ser Ser Arg Ala Ile Phe
530                 535                 540                 545 acc act ggc cag ggg gcg tcg gct gtg ggc ctc acg gcg tat gtc cag    1740
Thr Thr Gly Gln Gly Ala Ser Ala Val Gly Leu Thr Ala Tyr Val Gln
            550                 555                 560 cgg cac cct gtc agc agg gag tgg acc ttg gag gct ggg gcc ctg gtt    1788
Arg His Pro Val Ser Arg Glu Trp Thr Leu Glu Ala Gly Ala Leu Val
        565                 570                 575 ctg gct gac cga gga gtg tgt ctc att gat gaa ttt gac aag atg aat    1836
Leu Ala Asp Arg Gly Val Cys Leu Ile Asp Glu Phe Asp Lys Met Asn
    580                 585                 590 gac cag gac aga acc agc atc cat gag gcc atg gag caa cag agc atc    1884
Asp Gln Asp Arg Thr Ser Ile His Glu Ala Met Glu Gln Gln Ser Ile
595                 600                 605 tcc atc tcg aag gct ggc atc gtc acc tcc ctg cag gct cgc tgc acg    1932
Ser Ile Ser Lys Ala Gly Ile Val Thr Ser Leu Gln Ala Arg Cys Thr
610                 615                 620                 625 gtc att gct gcc gcc aac ccc ata gga ggg cgc tac gac ccc tcg ctg    1980
Val Ile Ala Ala Ala Asn Pro Ile Gly Gly Arg Tyr Asp Pro Ser Leu
            630                 635                 640 act ttc tct gag aac gtg gac ctc aca gag ccc atc atc tca cgc ttt    2028
Thr Phe Ser Glu Asn Val Asp Leu Thr Glu Pro Ile Ile Ser Arg Phe
        645                 650                 655 gac atc ctg tgt gtg gtg agg gac acc gtg gac cca gtc cag gac gag    2076
Asp Ile Leu Cys Val Val Arg Asp Thr Val Asp Pro Val Gln Asp Glu
    660                 665                 670 atg ctg gcc cgc ttc gtg gtg ggc agc cac gtc aga cac cac ccc agc    2124
Met Leu Ala Arg Phe Val Val Gly Ser His Val Arg His His Pro Ser
675                 680                 685 aac aag gag gag gag ggg ctg gcc aat ggc agc gct gct gag ccc gcc    2172
Asn Lys Glu Glu Glu Gly Leu Ala Asn Gly Ser Ala Ala Glu Pro Ala
690                 695                 700                 705 atg ccc aac acg tat ggc gtg gag ccc ctg ccc cag gag gtc ctg aag    2220
Met Pro Asn Thr Tyr Gly Val Glu Pro Leu Pro Gln Glu Val Leu Lys
            710                 715                 720 aag tac atc atc tac gcc aag gag agg gtc cac ccg aag ctc aac cag    2268
Lys Tyr Ile Ile Tyr Ala Lys Glu Arg Val His Pro Lys Leu Asn Gln
        725                 730                 735 atg gac cag gac aag gtg gcc aag atg tac agt gac ctg agg aaa gaa    2316
```

-continued

```
Met Asp Gln Asp Lys Val Ala Lys Met Tyr Ser Asp Leu Arg Lys Glu
        740                 745                 750 tct atg gcg aca ggc agc atc ccc att acg gtg cgg cac atc gag tcc    2364
Ser Met Ala Thr Gly Ser Ile Pro Ile Thr Val Arg His Ile Glu Ser
755                 760                 765 atg atc cgc atg gcg gag gcc cac gcg cgc atc cat ctg cgg gac tat    2412
Met Ile Arg Met Ala Glu Ala His Ala Arg Ile His Leu Arg Asp Tyr
770                 775                 780                 785 gtg atc gaa gac gac gtc aac atg gcc atc cgc gtg atg ctg gag agc    2460
Val Ile Glu Asp Asp Val Asn Met Ala Ile Arg Val Met Leu Glu Ser
                790                 795                 800 ttc ata gac aca cag aag ttc agc gtc atg cgc agc atg cgc aag act    2508
Phe Ile Asp Thr Gln Lys Phe Ser Val Met Arg Ser Met Arg Lys Thr
            805                 810                 815 ttt gcc cgc tac ctt tca ttc cgg cgt gac aac aat gag ctg ttg ctc    2556
Phe Ala Arg Tyr Leu Ser Phe Arg Arg Asp Asn Asn Glu Leu Leu Leu
        820                 825                 830 ttc ata ctg aag cag tta gtg gca gag cag gtg aca tat cag cgc aac    2604
Phe Ile Leu Lys Gln Leu Val Ala Glu Gln Val Thr Tyr Gln Arg Asn
835                 840                 845 cgc ttt ggg gcc cag cag gac act att gag gtc cct gag aag gac ttg    2652
Arg Phe Gly Ala Gln Gln Asp Thr Ile Glu Val Pro Glu Lys Asp Leu
850                 855                 860                 865 gtg gat aag gct cgt cag atc aac atc cac aac ctc tct gca ttt tat    2700
Val Asp Lys Ala Arg Gln Ile Asn Ile His Asn Leu Ser Ala Phe Tyr
                870                 875                 880 gac agt gag ctc ttc agg atg aac aag ttc agc cac gac ctg aaa agg    2748
Asp Ser Glu Leu Phe Arg Met Asn Lys Phe Ser His Asp Leu Lys Arg
            885                 890                 895 aaa atg atc ctg cag cag ttc tga ggccctatgc catccataag gattccttgg   2802
Lys Met Ile Leu Gln Gln Phe  *
        900 gattctggtt tggggtggtc agtgccctct gtgctttatg gacacaaaac cagagcactt   2862 gatgaactcg gggtactagg gtcagggctt atagcaggat gtctggctgc acctggcatg   2922 actgtttgtt tctccaagcc tgctttgtgc ttctcacctt tgggtgggat gccttgccag   2982 tgtgtcttac ttggttgctg aacatcttgc cacctccgag tgctttgtct ccactcagta   3042 ccttggatca gagctgctga gttcaggatg cctgcgtgtg gtttaggtgt tagccttctt   3102 acatggatgt caggagagct gctgccctct tggcgtgagt tgcgtattca ggctgctttt   3162 gctgcctttg ccagagagc tggttgaaga tgtttgtaat cgttttcagt ctcctgcagg    3222 tttctgtgcc cctgtggtgg aagagggcac gacagtgcca gcgcagcgtt ctgggctcct   3282 cagtcgcagg ggtgggatgt gagtcatgcg gattatccac tcgccacagt tatcagctgc   3342 cattgctccc tgtctgtttc cccactctct tatttgtgca ttcggtttgg tttctgtagt   3402 tttaattttt aataaagttg aataaaatat aaaaaaaaaa aaaaaaaaa a            3453

<210> SEQ ID NO 3
<211> LENGTH: 14
<212> TYPE: PRT
<213> ORGANISM: Artificial Sequence
<220> FEATURE:
<223> OTHER INFORMATION: Amino acid sequence for the MCM2 epitope of
      monoclonal antibody 27C5.6

<400> SEQUENCE: 3

Ile Tyr Gln Asn Tyr Gln Arg Ile Arg Ile Gln Glu Ser Pro
1               5                   10
```

<210> SEQ ID NO 4
<211> LENGTH: 23
<212> TYPE: PRT
<213> ORGANISM: Artificial Sequence
<220> FEATURE:
<223> OTHER INFORMATION: Amino acid sequence for the MCM2 epitope of
monoclonal antibody 26H6.19 (preliminary)

<400> SEQUENCE: 4

Pro Ser Asn Lys Glu Glu Glu Gly Leu Ala Asn Gly Ser Ala Ala Glu
1               5                   10                  15

Pro Ala Met Pro Asn Thr Tyr
            20

<210> SEQ ID NO 5
<211> LENGTH: 2688
<212> TYPE: DNA
<213> ORGANISM: Artificial Sequence
<220> FEATURE:
<223> OTHER INFORMATION: Nucleotide sequence for truncated MCM2 gene
<220> FEATURE:
<221> NAME/KEY: CDS
<222> LOCATION: (1)...(2688)
<223> OTHER INFORMATION: Truncated MCM2 gene lacking 27 bp at 5' end

<400> SEQUENCE: 5

```
atg gca tcc agc ccg gcc cag cgt cgg cga ggc aat gat cct ctc acc        48
Met Ala Ser Ser Pro Ala Gln Arg Arg Arg Gly Asn Asp Pro Leu Thr
 1               5                  10                  15 tcc agc cct ggc cga agc tcc cgg cgt act gat gcc ctc acc tcc agc        96
Ser Ser Pro Gly Arg Ser Ser Arg Arg Thr Asp Ala Leu Thr Ser Ser
            20                  25                  30 cct ggc cgt gac ctt cca cca ttt gag gat gag tcc gag ggg ctc cta       144
Pro Gly Arg Asp Leu Pro Pro Phe Glu Asp Glu Ser Glu Gly Leu Leu
        35                  40                  45 ggc aca gag ggg ccc ctg gag gaa gaa gag gat gga gag gag ctc att       192
Gly Thr Glu Gly Pro Leu Glu Glu Glu Glu Asp Gly Glu Glu Leu Ile
    50                  55                  60 gga gat ggc atg gaa agg gac tac cgc gcc atc cca gag ctg gac gcc       240
Gly Asp Gly Met Glu Arg Asp Tyr Arg Ala Ile Pro Glu Leu Asp Ala
65                  70                  75                  80 tat gag gcc gag gga ctg gct ctg gat gat gag gac gta gag gag ctg       288
Tyr Glu Ala Glu Gly Leu Ala Leu Asp Asp Glu Asp Val Glu Glu Leu
                85                  90                  95 acg gcc agt cag agg gag gca gca gag cgg gcc atg cgg cag cgt gac       336
Thr Ala Ser Gln Arg Glu Ala Ala Glu Arg Ala Met Arg Gln Arg Asp
            100                 105                 110 cgg gag gct ggc cgg ggc ctg ggc cgc atg cgc cgt ggg ctc ctg tat       384
Arg Glu Ala Gly Arg Gly Leu Gly Arg Met Arg Arg Gly Leu Leu Tyr
        115                 120                 125 gac agc gat gag gag gac gag gag cgc cct gcc cgc aag cgc gcc cag       432
Asp Ser Asp Glu Glu Asp Glu Glu Arg Pro Ala Arg Lys Arg Arg Gln
    130                 135                 140 gtg gag cgg gcc acg gag gac ggc gag gag gac gag gag atg atc gag       480
Val Glu Arg Ala Thr Glu Asp Gly Glu Glu Asp Glu Glu Met Ile Glu
145                 150                 155                 160 agc atc gag aac ctg gag gat ctc aaa ggc cac tct gtg cgc gag tgg       528
Ser Ile Glu Asn Leu Glu Asp Leu Lys Gly His Ser Val Arg Glu Trp
                165                 170                 175 gtg agc atg gcg ggc ccc cgg ctg gag atc cac cac cgc ttc aag aac       576
Val Ser Met Ala Gly Pro Arg Leu Glu Ile His His Arg Phe Lys Asn
            180                 185                 190
```

| | | |
|---|---|---|
| ttc ctg cgc act cac gtc gac agc cac ggc cac aac gtc ttc aag gag<br>Phe Leu Arg Thr His Val Asp Ser His Gly His Asn Val Phe Lys Glu<br>            195                      200                  205 | 624 |

```
ttc ctg cgc act cac gtc gac agc cac ggc cac aac gtc ttc aag gag    624
Phe Leu Arg Thr His Val Asp Ser His Gly His Asn Val Phe Lys Glu
            195                 200                 205 cgc atc agc gac atg tgc aaa gag aac cgt gag agc ctg gtg gtg aac    672
Arg Ile Ser Asp Met Cys Lys Glu Asn Arg Glu Ser Leu Val Val Asn
        210                 215                 220 tat gag gac ttg gca gcc agg gag cac gtg ctg gcc tac ttc ctg cct    720
Tyr Glu Asp Leu Ala Ala Arg Glu His Val Leu Ala Tyr Phe Leu Pro
225                 230                 235                 240 gag gca ccg gcg gag ctg ctg cag atc ttt gat gag gct gcc ctg gag    768
Glu Ala Pro Ala Glu Leu Leu Gln Ile Phe Asp Glu Ala Ala Leu Glu
            245                 250                 255 gtg gta ctg gcc atg tac ccc aag tac gac cgc atc acc aac cac atc    816
Val Val Leu Ala Met Tyr Pro Lys Tyr Asp Arg Ile Thr Asn His Ile
        260                 265                 270 cat gtc cgc atc tcc cac ctg cct ctg gtg gag gag ctg cgc tcg ctg    864
His Val Arg Ile Ser His Leu Pro Leu Val Glu Glu Leu Arg Ser Leu
    275                 280                 285 agg cag ctg cat ctg aac cag ctg atc cgc acc agt ggg gtg gtg acc    912
Arg Gln Leu His Leu Asn Gln Leu Ile Arg Thr Ser Gly Val Val Thr
            290                 295                 300 agc tgc act ggc gtc ctg ccc cag ctc agc atg gtc aag tac aac tgc    960
Ser Cys Thr Gly Val Leu Pro Gln Leu Ser Met Val Lys Tyr Asn Cys
305                 310                 315                 320 aac aag tgc aat ttc gtc ctg ggt cct ttc tgc cag tcc cag aac cag   1008
Asn Lys Cys Asn Phe Val Leu Gly Pro Phe Cys Gln Ser Gln Asn Gln
            325                 330                 335 gag gtg aaa cca ggc tcc tgt cct gag tgc cag tcg gcc ggc ccc ttt   1056
Glu Val Lys Pro Gly Ser Cys Pro Glu Cys Gln Ser Ala Gly Pro Phe
        340                 345                 350 gag gtc aac atg gag gag acc atc tat cag aac tac cag cgt atc cga   1104
Glu Val Asn Met Glu Glu Thr Ile Tyr Gln Asn Tyr Gln Arg Ile Arg
    355                 360                 365 atc cag gag agt cca ggc aaa gtg gcg gct ggc cgg ctg ccc cgc tcc   1152
Ile Gln Glu Ser Pro Gly Lys Val Ala Ala Gly Arg Leu Pro Arg Ser
            370                 375                 380 aag gac gcc att ctc ctc gca gat ctg gtg gac agc tgc aag cca gga   1200
Lys Asp Ala Ile Leu Leu Ala Asp Leu Val Asp Ser Cys Lys Pro Gly
385                 390                 395                 400 gac gag ata gag ctg act ggc atc tat cac aac aac tat gat ggc tcc   1248
Asp Glu Ile Glu Leu Thr Gly Ile Tyr His Asn Asn Tyr Asp Gly Ser
            405                 410                 415 ctc aac act gcc aat ggc ttc cct gtc ttt gcc act gtc atc cta gcc   1296
Leu Asn Thr Ala Asn Gly Phe Pro Val Phe Ala Thr Val Ile Leu Ala
        420                 425                 430 aac cac gtg gcc aag aag gac aac aag gtt gct gta ggg gaa ctg acc   1344
Asn His Val Ala Lys Lys Asp Asn Lys Val Ala Val Gly Glu Leu Thr
    435                 440                 445 gat gaa gat gtg aag atg atc act agc ctc tcc aag gat cag cag atc   1392
Asp Glu Asp Val Lys Met Ile Thr Ser Leu Ser Lys Asp Gln Gln Ile
450                 455                 460 gga gag aag atc ttt gcc agc att gct cct tcc atc tat ggt cat gaa   1440
Gly Glu Lys Ile Phe Ala Ser Ile Ala Pro Ser Ile Tyr Gly His Glu
465                 470                 475                 480 gac atc aag aga ggc ctg gct ctg gcc ctg ttc gga ggg gag ccc aaa   1488
Asp Ile Lys Arg Gly Leu Ala Leu Ala Leu Phe Gly Gly Glu Pro Lys
            485                 490                 495 aac cca ggt ggc aag cac aag gta cgt ggt gat atc aac gtg ctc ttg   1536
Asn Pro Gly Gly Lys His Lys Val Arg Gly Asp Ile Asn Val Leu Leu
        500                 505                 510
```

```
                                    -continued tgc gga gac cct ggc aca gcg aag tcg cag ttt ctc aag tat att gag    1584
Cys Gly Asp Pro Gly Thr Ala Lys Ser Gln Phe Leu Lys Tyr Ile Glu
        515                 520                 525 aaa gtg tcc agc cga gcc atc ttc acc act ggc cag ggg gcg tcg gct    1632
Lys Val Ser Ser Arg Ala Ile Phe Thr Thr Gly Gln Gly Ala Ser Ala
530                 535                 540 gtg ggc ctc acg gcg tat gtc cag cgg cac cct gtc agc agg gag tgg    1680
Val Gly Leu Thr Ala Tyr Val Gln Arg His Pro Val Ser Arg Glu Trp
545                 550                 555                 560 acc ttg gag gct ggg gcc ctg gtt ctg gct gac cga gga gtg tgt ctc    1728
Thr Leu Glu Ala Gly Ala Leu Val Leu Ala Asp Arg Gly Val Cys Leu
                565                 570                 575 att gat gaa ttt gac aag atg aat gac cag gac aga acc agc atc cat    1776
Ile Asp Glu Phe Asp Lys Met Asn Asp Gln Asp Arg Thr Ser Ile His
            580                 585                 590 gag gcc atg gag caa cag agc atc tcc atc tcg aag gct ggc atc gtc    1824
Glu Ala Met Glu Gln Gln Ser Ile Ser Ile Ser Lys Ala Gly Ile Val
        595                 600                 605 acc tcc ctg cag gct cgc tgc acg gtc att gct gcc gcc aac ccc ata    1872
Thr Ser Leu Gln Ala Arg Cys Thr Val Ile Ala Ala Ala Asn Pro Ile
610                 615                 620 gga ggg cgc tac gac ccc tcg ctg act ttc tct gag aac gtg gac ctc    1920
Gly Gly Arg Tyr Asp Pro Ser Leu Thr Phe Ser Glu Asn Val Asp Leu
625                 630                 635                 640 aca gag ccc atc atc tca cgc ttt gac atc ctg tgt gtg gtg agg gac    1968
Thr Glu Pro Ile Ile Ser Arg Phe Asp Ile Leu Cys Val Val Arg Asp
                645                 650                 655 acc gtg gac cca gtc cag gac gag atg ctg gcc cgc ttc gtg gtg ggc    2016
Thr Val Asp Pro Val Gln Asp Glu Met Leu Ala Arg Phe Val Val Gly
            660                 665                 670 agc cac gtc aga cac cac ccc agc aac aag gag gag gag ggg ctg gcc    2064
Ser His Val Arg His His Pro Ser Asn Lys Glu Glu Glu Gly Leu Ala
        675                 680                 685 aat ggc agc gct gct gag ccc gcc atg ccc aac acg tat ggc gtg gag    2112
Asn Gly Ser Ala Ala Glu Pro Ala Met Pro Asn Thr Tyr Gly Val Glu
690                 695                 700 ccc ctg ccc cag gag gtc ctg aag aag tac atc atc tac gcc aag gag    2160
Pro Leu Pro Gln Glu Val Leu Lys Lys Tyr Ile Ile Tyr Ala Lys Glu
705                 710                 715                 720 agg gtc cac ccg aag ctc aac cag atg gac cag gac aag gtg gcc aag    2208
Arg Val His Pro Lys Leu Asn Gln Met Asp Gln Asp Lys Val Ala Lys
                725                 730                 735 atg tac agt gac ctg agg aaa gaa tct atg gcg aca ggc agc atc ccc    2256
Met Tyr Ser Asp Leu Arg Lys Glu Ser Met Ala Thr Gly Ser Ile Pro
            740                 745                 750 att acg gtg cgg cac atc gag tcc atg atc cgc atg gcg gag gcc cac    2304
Ile Thr Val Arg His Ile Glu Ser Met Ile Arg Met Ala Glu Ala His
        755                 760                 765 gcg cgc atc cat ctg cgg gac tat gtg atc gaa gac gac gtc aac atg    2352
Ala Arg Ile His Leu Arg Asp Tyr Val Ile Glu Asp Asp Val Asn Met
770                 775                 780 gcc atc cgc gtg atg ctg gag agc ttc ata gac aca cag aag ttc agc    2400
Ala Ile Arg Val Met Leu Glu Ser Phe Ile Asp Thr Gln Lys Phe Ser
785                 790                 795                 800 gtc atg cgc agc atg cgc aag act ttt gcc cgc tac ctt tca ttc cgg    2448
Val Met Arg Ser Met Arg Lys Thr Phe Ala Arg Tyr Leu Ser Phe Arg
                805                 810                 815 cgt gac aac aat gag ctg ttg ctc ttc ata ctg aag cag tta gtg gca    2496
Arg Asp Asn Asn Glu Leu Leu Leu Phe Ile Leu Lys Gln Leu Val Ala
```

-continued

```
                    820                 825                 830
gag cag gtg aca tat cag cgc aac cgc ttt ggg gcc cag cag gac act    2544
Glu Gln Val Thr Tyr Gln Arg Asn Arg Phe Gly Ala Gln Gln Asp Thr
                835                 840                 845 att gag gtc cct gag aag gac ttg gtg gat aag gct cgt cag atc aac    2592
Ile Glu Val Pro Glu Lys Asp Leu Val Asp Lys Ala Arg Gln Ile Asn
    850                 855                 860 atc cac aac ctc tct gca ttt tat gac agt gag ctc ttc agg atg aac    2640
Ile His Asn Leu Ser Ala Phe Tyr Asp Ser Glu Leu Phe Arg Met Asn
865                 870                 875                 880 aag ttc agc cac gac ctg aaa agg aaa atg atc ctg cag cag ttc tga    2688
Lys Phe Ser His Asp Leu Lys Arg Lys Met Ile Leu Gln Gln Phe  *
                885                 890                 895

<210> SEQ ID NO 6
<211> LENGTH: 27
<212> TYPE: DNA
<213> ORGANISM: Artificial Sequence
<220> FEATURE:
<223> OTHER INFORMATION: 5' nucleotide sequence omitted from truncated
      MCM2 nucleotide sequence

<400> SEQUENCE: 6
atggcggaat catcggaatc cttcacc                                        27

<210> SEQ ID NO 7
<211> LENGTH: 28
<212> TYPE: PRT
<213> ORGANISM: Artificial Sequence
<220> FEATURE:
<223> OTHER INFORMATION: MCM2 fragment corresponding to amino acid
      residues 355 to 382 of SEQ ID NO:1

<400> SEQUENCE: 7

Cys Gln Ser Ala Gly Pro Phe Glu Val Asn Met Glu Glu Thr Ile Tyr
1               5                   10                  15

Gln Asn Tyr Gln Arg Ile Arg Ile Gln Glu Ser Pro
            20                  25

<210> SEQ ID NO 8
<211> LENGTH: 14
<212> TYPE: PRT
<213> ORGANISM: Artificial Sequence
<220> FEATURE:
<223> OTHER INFORMATION: MCM2 fragment corresponding to amino acid
      residues 355 to 368 of SEQ ID NO:1

<400> SEQUENCE: 8

Cys Gln Ser Ala Gly Pro Phe Glu Val Asn Met Glu Glu Thr
1               5                   10

<210> SEQ ID NO 9
<211> LENGTH: 14
<212> TYPE: PRT
<213> ORGANISM: Artificial Sequence
<220> FEATURE:
<223> OTHER INFORMATION: MCM2 fragment corresponding to amino acid
      residues 362 to 375 of SEQ ID NO:1

<400> SEQUENCE: 9

Glu Val Asn Met Glu Glu Thr Ile Tyr Gln Asn Tyr Gln Arg
1               5                   10

<210> SEQ ID NO 10
<211> LENGTH: 2718
```

```
<212> TYPE: DNA
<213> ORGANISM: Artificial Sequence
<220> FEATURE:
<223> OTHER INFORMATION: Nucleotide sequence encoding the hexa-histidine
      tagged MCM2 immunogenic polypeptide
<220> FEATURE:
<221> NAME/KEY: misc_feature
<222> LOCATION: (2698)...(2715)
<223> OTHER INFORMATION: Nucleotide sequence encoding hexa-histidine tag

<400> SEQUENCE: 10
atggcatcca gcccggccca gcgtcggcga ggcaatgatc ctctcacctc cagccctggc     60
cgaagctccc ggcgtactga tgccctcacc tccagccctg gccgtgacct tccaccattt    120
gaggatgagt ccgaggggct cctaggcaca gaggggcccc tggaggaaga gaggatgga    180
gaggagctca ttggagatgg catggaaagg gactaccgcg ccatcccaga gctggacgcc    240
tatgaggccg agggactggc tctggatgat gaggacgtag aggagctgac ggccagtcag    300
agggaggcag cagagcgggc catgcggcag cgtgaccggg aggctggccg gggcctgggc    360
cgcatgcgcc gtgggctcct gtatgacagc gatgaggagg acgaggagcg ccctgcccgc    420
aagcgccgcc aggtggagcg ggccacggag gacggcgagg aggacgagga gatgattgag    480
agcatcgaga acctggagga tctcaaaggc cactctgtgc gcgagtgggt gagcatggcg    540
ggccccggc tggagatcca ccaccgcttc aagaacttcc tgcgcactca cgtcgacagc    600
cacggccaca acgtcttcaa ggagcgcatc agcgacatgt gcaaagagaa ccgtgagagc    660
ctggtggtga actatgagga cttggcagcc agggagcacg tgctggccta cttcctgcct    720
gaggcaccgg cggagctgct gcagatctt gatgaggctg ccctggaggt ggtactggcc    780
atgtacccca gtacgaccg catcaccaac cacatccatg tccgcatctc ccacctgcct    840
ctggtggagg agctgcgctc gctgaggcag ctgcatctga accagctgat ccgcaccagt    900
gggggtggtga ccagctgcac tggcgtcctg ccccagctca gcatggtcaa gtacaactgc    960
aacaagtgca atttcgtcct gggtccttc tgccagtccc agaaccagga ggtgaaacca   1020
ggctcctgtc ctgagtgcca gtcggccggc ccctttgagg tcaacatgga ggagaccatc   1080
tatcagaact accagcgtat ccgaatccag gagagtccag gcaaagtggc ggctggccgg   1140
ctgccccgct ccaaggacgc cattctcctc gcagatctgg tggacagctg caagccagga   1200
gacgagatag agctgactgg catctatcac aacaactatg atggctccct caacactgcc   1260
aatggcttcc ctgtctttgc cactgtcatc ctagccaacc acgtggccaa gaaggacaac   1320
aaggttgctg taggggaact gaccgatgaa gatgtgaaga tgatcactag cctctccaag   1380
gatcagcaga tcggagagaa gatctttgcc agcattgctc cttccatcta tggtcatgaa   1440
gacatcaaga gaggcctggc tctggcctg ttcggagggg agcccaaaaa cccaggtggc   1500
aagcacaagg tacgtggtga tatcaacgtg ctcttgtgcg agaccctgg cacagcgaag   1560
tcgcagtttc tcaagtatat tgagaaagtg tccagccgag ccatcttcac cactggccag   1620
ggggcgtcgg ctgtgggcct cacggcgtat gtccagcggc accctgtcag cagggagtgg   1680
accttggagg ctggggccct ggttctggct gaccgaggag tgtgtctcat tgatgaattt   1740
gacaagatga atgaccagga cagaaccagc atccatgagg ccatggagca acagagcatc   1800
tccatctcga aggctggcat cgtcacctcc ctgcaggctc gctgcacggt cattgctgcc   1860
gccaaccca taggagggcg ctacgacccc tcgctgactt tctctgagaa cgtggacctc   1920
acagagccca tcatctcacg ctttgacatc ctgtgtgtgg tgagggacac cgtgacccca   1980
gtccaggacg agatgctggc ccgcttcgtg gtgggcagcc acgtcagaca ccaccccagc   2040
```

-continued

```
aacaaggagg aggagggct ggccaatggc agcgctgctg agcccgccat gcccaacacg    2100
tatggcgtgg agcccctgcc ccaggaggtc ctgaagaagt acatcatcta cgccaaggag    2160
agggtccacc cgaagctcaa ccagatggac caggacaagg tggccaagat gtacagtgac    2220
ctgaggaaag aatctatggc gacaggcagc atccccatta cggtgcggca catcgagtcc    2280
atgatccgca tggcggaggc ccacgcgcgc atccatctgc gggactatgt gatcgaagac    2340
gacgtcaaca tggccatccg cgtgatgctg gagagcttca tagacacaca aagttcagc     2400 gtcatgcgca gcatgcgcaa gacttttgcc cgctacctttt cattccggcg tgacaacaat    2460
gagctgttgc tcttcatact gaagcagtta gtggcagagc aggtgacata tcagcgcaac    2520
cgctttgggg cccagcagga cactattgag gtccctgaga aggacttggt ggataaggct    2580
cgtcagatca acatccacaa cctctctgca ttttatgaca gtgagctctt caggatgaac    2640
aagttcagcc acgacctgaa aaggaaaatg atcctgcagc agttcctcga gggtggtcat    2700
catcatcatc atcattga                                                  2718
```

<210> SEQ ID NO 11
<211> LENGTH: 905
<212> TYPE: PRT
<213> ORGANISM: Artificial Sequence
<220> FEATURE:
<223> OTHER INFORMATION: Amino acid sequence for hexa-histidine tagged
      MCM2 immunogenic polypeptide
<220> FEATURE:
<223> OTHER INFORMATION: Hexa-histidine tag

<400> SEQUENCE: 11

```
Met Ala Ser Ser Pro Ala Gln Arg Arg Gly Asn Asp Pro Leu Thr
 1               5                  10                  15

Ser Ser Pro Gly Arg Ser Ser Arg Arg Thr Asp Ala Leu Thr Ser Ser
                20                  25                  30

Pro Gly Arg Asp Leu Pro Pro Phe Glu Asp Glu Ser Glu Gly Leu Leu
            35                  40                  45

Gly Thr Glu Gly Pro Leu Glu Glu Glu Glu Asp Gly Glu Glu Leu Ile
        50                  55                  60

Gly Asp Gly Met Glu Arg Asp Tyr Arg Ala Ile Pro Glu Leu Asp Ala
65                  70                  75                  80

Tyr Glu Ala Glu Gly Leu Ala Leu Asp Asp Glu Asp Val Glu Glu Leu
                85                  90                  95

Thr Ala Ser Gln Arg Glu Ala Ala Glu Arg Ala Met Arg Gln Arg Asp
            100                 105                 110

Arg Glu Ala Gly Arg Gly Leu Gly Arg Met Arg Arg Gly Leu Leu Tyr
        115                 120                 125

Asp Ser Asp Glu Glu Asp Glu Glu Arg Pro Ala Arg Lys Arg Arg Gln
    130                 135                 140

Val Glu Arg Ala Thr Glu Asp Gly Glu Glu Asp Glu Glu Met Ile Glu
145                 150                 155                 160

Ser Ile Glu Asn Leu Glu Asp Leu Lys Gly His Ser Val Arg Glu Trp
                165                 170                 175

Val Ser Met Ala Gly Pro Arg Leu Glu Ile His His Arg Phe Lys Asn
            180                 185                 190

Phe Leu Arg Thr His Val Asp Ser His Gly His Asn Val Phe Lys Glu
        195                 200                 205

Arg Ile Ser Asp Met Cys Lys Glu Asn Arg Glu Ser Leu Val Val Asn
    210                 215                 220
```

```
Tyr Glu Asp Leu Ala Ala Arg Glu His Val Leu Ala Tyr Phe Leu Pro
225                 230                 235                 240

Glu Ala Pro Ala Glu Leu Leu Gln Ile Phe Asp Glu Ala Ala Leu Glu
            245                 250                 255

Val Val Leu Ala Met Tyr Pro Lys Tyr Asp Arg Ile Thr Asn His Ile
                260                 265                 270

His Val Arg Ile Ser His Leu Pro Leu Val Glu Leu Arg Ser Leu
        275                 280                 285

Arg Gln Leu His Leu Asn Gln Leu Ile Arg Thr Ser Gly Val Val Thr
    290                 295                 300

Ser Cys Thr Gly Val Leu Pro Gln Leu Ser Met Val Lys Tyr Asn Cys
305                 310                 315                 320

Asn Lys Cys Asn Phe Val Leu Gly Pro Phe Cys Gln Ser Gln Asn Gln
                325                 330                 335

Glu Val Lys Pro Gly Ser Cys Pro Glu Cys Gln Ser Ala Gly Pro Phe
                340                 345                 350

Glu Val Asn Met Glu Glu Thr Ile Tyr Gln Asn Tyr Gln Arg Ile Arg
                355                 360                 365

Ile Gln Glu Ser Pro Gly Lys Val Ala Ala Gly Arg Leu Pro Arg Ser
    370                 375                 380

Lys Asp Ala Ile Leu Leu Ala Asp Leu Val Asp Ser Cys Lys Pro Gly
385                 390                 395                 400

Asp Glu Ile Glu Leu Thr Gly Ile Tyr His Asn Asn Tyr Asp Gly Ser
                405                 410                 415

Leu Asn Thr Ala Asn Gly Phe Pro Val Phe Ala Thr Val Ile Leu Ala
                420                 425                 430

Asn His Val Ala Lys Lys Asp Asn Lys Val Ala Val Gly Glu Leu Thr
        435                 440                 445

Asp Glu Asp Val Lys Met Ile Thr Ser Leu Ser Lys Asp Gln Gln Ile
450                 455                 460

Gly Glu Lys Ile Phe Ala Ser Ile Ala Pro Ser Ile Tyr Gly His Glu
465                 470                 475                 480

Asp Ile Lys Arg Gly Leu Ala Leu Ala Leu Phe Gly Gly Glu Pro Lys
                485                 490                 495

Asn Pro Gly Gly Lys His Lys Val Arg Gly Asp Ile Asn Val Leu Leu
                500                 505                 510

Cys Gly Asp Pro Gly Thr Ala Lys Ser Gln Phe Leu Lys Tyr Ile Glu
                515                 520                 525

Lys Val Ser Ser Arg Ala Ile Phe Thr Thr Gly Gln Gly Ala Ser Ala
530                 535                 540

Val Gly Leu Thr Ala Tyr Val Gln Arg His Pro Val Ser Arg Glu Trp
545                 550                 555                 560

Thr Leu Glu Ala Gly Ala Leu Val Leu Ala Asp Arg Gly Val Cys Leu
                565                 570                 575

Ile Asp Glu Phe Asp Lys Met Asn Asp Gln Asp Arg Thr Ser Ile His
                580                 585                 590

Glu Ala Met Glu Gln Gln Ser Ile Ser Ile Ser Lys Ala Gly Ile Val
            595                 600                 605

Thr Ser Leu Gln Ala Arg Cys Thr Val Ile Ala Ala Asn Pro Ile
        610                 615                 620

Gly Gly Arg Tyr Asp Pro Ser Leu Thr Phe Ser Glu Asn Val Asp Leu
625                 630                 635                 640
```

```
Thr Glu Pro Ile Ile Ser Arg Phe Asp Ile Leu Cys Val Val Arg Asp
                645                 650                 655

Thr Val Asp Pro Val Gln Asp Glu Met Leu Ala Arg Phe Val Val Gly
            660                 665                 670

Ser His Val Arg His His Pro Ser Asn Lys Glu Glu Gly Leu Ala
        675                 680                 685

Asn Gly Ser Ala Ala Glu Pro Ala Met Pro Asn Thr Tyr Gly Val Glu
    690                 695                 700

Pro Leu Pro Gln Glu Val Leu Lys Lys Tyr Ile Ile Tyr Ala Lys Glu
705                 710                 715                 720

Arg Val His Pro Lys Leu Asn Gln Met Asp Gln Lys Val Ala Lys
                725                 730                 735

Met Tyr Ser Asp Leu Arg Lys Glu Ser Met Ala Thr Gly Ser Ile Pro
                740                 745                 750

Ile Thr Val Arg His Ile Glu Ser Met Ile Arg Met Ala Glu Ala His
            755                 760                 765

Ala Arg Ile His Leu Arg Asp Tyr Val Ile Glu Asp Val Asn Met
770                 775                 780

Ala Ile Arg Val Met Leu Glu Ser Phe Ile Asp Thr Gln Lys Phe Ser
785                 790                 795                 800

Val Met Arg Ser Met Arg Lys Thr Phe Ala Arg Tyr Leu Ser Phe Arg
                805                 810                 815

Arg Asp Asn Asn Glu Leu Leu Leu Phe Ile Leu Lys Gln Leu Val Ala
                820                 825                 830

Glu Gln Val Thr Tyr Gln Arg Asn Arg Phe Gly Ala Gln Gln Asp Thr
            835                 840                 845

Ile Glu Val Pro Glu Lys Asp Leu Val Asp Lys Ala Arg Gln Ile Asn
    850                 855                 860

Ile His Asn Leu Ser Ala Phe Tyr Asp Ser Glu Leu Phe Arg Met Asn
865                 870                 875                 880

Lys Phe Ser His Asp Leu Lys Arg Lys Met Ile Leu Gln Gln Phe Leu
                885                 890                 895

Glu Gly Gly His His His His His
                900                 905

<210> SEQ ID NO 12
<211> LENGTH: 2718
<212> TYPE: DNA
<213> ORGANISM: Artificial Sequence
<220> FEATURE:
<223> OTHER INFORMATION: Nucleotide sequence encoding the MCM2-FLAG
      polypeptide

<400> SEQUENCE: 12
atggcatcca gcccggccca gcgtcggcga ggcaatgatc ctctcacctc cagccctggc      60
cgaagctccc ggcgtactga tgccctcacc tccagccctg ccgtgacct tccaccattt     120 gaggatgagt ccgaggggct cctaggcaca gaggggcccc tggaggaaga agaggatgga     180
gaggagctca ttggagatgg catggaaagg gactaccgcg ccatcccaga gctggacgcc     240
tatgaggccg agggactggc tctggatgat gaggacgtag aggagctgac ggccagtcag     300
agggaggcag cagagcgggc catgcggcag cgtgaccggg aggctggccg gggcctgggc     360
cgcatgcgcc gtgggctcct gtatgacagc gatgaggagg acgaggagcg ccctgcccgc     420
aagcgccgcc aggtggagcg ggccacggag acggcgaggg aggacgagga gatgattgag     480
agcatcgaga acctggagga tctcaaaggc cactctgtgc gcgagtgggt gagcatggcg     540
```

```
ggcccccggc tggagatcca ccaccgcttc aagaacttcc tgcgcactca cgtcgacagc    600
cacggccaca acgtcttcaa ggagcgcatc agcgacatgt gcaaagagaa ccgtgagagc    660
ctggtggtga actatgagga cttggcagcc agggagcacg tgctggccta cttcctgcct    720
gaggcaccgg cggagctgct gcagatcttt gatgaggctg ccctggaggt ggtactggcc    780
atgtacccca gtacgaccg catcaccaac cacatccatg tccgcatctc ccacctgcct     840
ctggtggagg agctgcgctc gctgaggcag ctgcatctga accagctgat ccgcaccagt    900
ggggtggtga ccagctgcac tggcgtcctg ccccagctca gcatggtcaa gtacaactgc    960
aacaagtgca atttcgtcct gggtcctttc tgccagtccc agaaccagga ggtgaaacca   1020
ggctcctgtc ctgagtgcca gtcggccggc ccctttgagg tcaacatgga ggagaccatc   1080
tatcagaact accagcgtat ccgaatccag gagagtccag gcaaagtggc ggctggccgg   1140
ctgccccgct ccaaggacgc cattctcctc gcagatctgg tggacagctg caagccagga   1200
gacgagatag agctgactgg catctatcac aacaactatg atggctccct caacactgcc   1260
aatggcttcc ctgtctttgc cactgtcatc ctagccaacc acgtggccaa gaggacaac    1320 aaggttgctg taggggaact gaccgatgaa gatgtgaaga tgatcactag cctctccaag   1380
gatcagcaga tcggagagaa gatctttgcc agcattgctc cttccatcta tggtcatgaa   1440
gacatcaaga gaggcctggc tctggccctg ttcgaggggg agcccaaaaa cccaggtggc   1500
aagcacaagg tacgtggtga tatcaacgtg ctcttgtgcg agaccctgg cacagcgaag    1560 tcgcagtttc tcaagtatat tgagaaagtg tccagccgag ccatcttcac cactggccag   1620
ggggcgtcgg ctgtgggcct cacggcgtat gtccagcggc accctgtcag cagggagtgg   1680
accttggagg ctggggccct ggttctggct gaccgaggag tgtgtctcat tgatgaattt   1740
gacaagatga atgaccagga cagaaccagc atccatgagg ccatggagca acagagcatc   1800
tccatctcga aggctggcat cgtcacctcc ctgcaggctc gctgcacggt cattgctgcc   1860 gccaaccca taggagggcg ctacgacccc tcgctgactt tctctgagaa cgtggacctc   1920
acagagccca tcatctcacg ctttgacatc ctgtgtgtgg tgagggacac cgtggaccca   1980
gtccaggacg agatgctggc ccgcttcgtg gtgggcagcc acgtcagaca ccaccccagc   2040
aacaaggagg aggagggct ggccaatggc agcgctgctg agcccgccat gcccaacacg   2100
tatggcgtgg agcccctgcc ccaggaggtc ctgaagaagt acatcatcta cgccaaggag   2160
agggtccacc cgaagctcaa ccagatggac caggacaagg tggccaagat gtacagtgac   2220
ctgaggaaag aatctatggc gacaggcagc atcccccatta cggtgcggca catcgagtcc   2280
atgatccgca tggcggaggc ccacgcgcgc atccatctgc gggactatgt gatcgaagac   2340
gacgtcaaca tggccatccg cgtgatgctg gagagcttca tagacacaca gaagttcagc   2400
gtcatgcgca gcatgcgcaa gacttttgcc cgctacctt cattccggcg tgacaacaat    2460
gagctgttgc tcttcatact gaagcagtta gtggcagagc aggtgacata tcagcgcaac   2520
cgctttgggg cccagcagga cactattgag gtccctgaga aggacttggt ggataaggct   2580
cgtcagatca acatccacaa cctctctgca ttttatgaca gtgagctctt caggatgaac   2640
aagttcagcc acgacctgaa aaggaaaatg atcctgcagc agttcctcga ggactacaaa   2700
gacgacgacg acaagtag                                                 2718
```

<210> SEQ ID NO 13
<211> LENGTH: 905
<212> TYPE: PRT

<213> ORGANISM: Artificial Sequence
<220> FEATURE:
<223> OTHER INFORMATION: Amino acid sequence for the MCM2-FLAG polypeptide

<400> SEQUENCE: 13

```
Met Ala Ser Ser Pro Ala Gln Arg Arg Arg Gly Asn Asp Pro Leu Thr
 1               5                  10                  15

Ser Ser Pro Gly Arg Ser Ser Arg Thr Asp Ala Leu Thr Ser Ser
            20                  25                  30

Pro Gly Arg Asp Leu Pro Pro Phe Glu Asp Glu Ser Glu Gly Leu Leu
            35                  40                  45

Gly Thr Glu Gly Pro Leu Glu Glu Glu Glu Asp Gly Glu Glu Leu Ile
 50                  55                  60

Gly Asp Gly Met Glu Arg Asp Tyr Arg Ala Ile Pro Glu Leu Asp Ala
 65                  70                  75                  80

Tyr Glu Ala Glu Gly Leu Ala Leu Asp Asp Glu Asp Val Glu Glu Leu
             85                  90                  95

Thr Ala Ser Gln Arg Glu Ala Ala Glu Arg Ala Met Arg Gln Arg Asp
             100                 105                 110

Arg Glu Ala Gly Arg Gly Leu Gly Arg Met Arg Arg Gly Leu Leu Tyr
             115                 120                 125

Asp Ser Asp Glu Glu Asp Glu Glu Arg Pro Ala Arg Lys Arg Arg Gln
 130                 135                 140

Val Glu Arg Ala Thr Glu Asp Gly Glu Glu Asp Glu Glu Met Ile Glu
145                 150                 155                 160

Ser Ile Glu Asn Leu Glu Asp Leu Lys Gly His Ser Val Arg Glu Trp
                165                 170                 175

Val Ser Met Ala Gly Pro Arg Leu Glu Ile His His Arg Phe Lys Asn
            180                 185                 190

Phe Leu Arg Thr His Val Asp Ser His Gly His Asn Val Phe Lys Glu
            195                 200                 205

Arg Ile Ser Asp Met Cys Lys Glu Asn Arg Glu Ser Leu Val Val Asn
210                 215                 220

Tyr Glu Asp Leu Ala Ala Arg Glu His Val Leu Ala Tyr Phe Leu Pro
225                 230                 235                 240

Glu Ala Pro Ala Glu Leu Leu Gln Ile Phe Asp Glu Ala Ala Leu Glu
                245                 250                 255

Val Val Leu Ala Met Tyr Pro Lys Tyr Asp Arg Ile Thr Asn His Ile
            260                 265                 270

His Val Arg Ile Ser His Leu Pro Leu Val Glu Glu Leu Arg Ser Leu
            275                 280                 285

Arg Gln Leu His Leu Asn Gln Leu Ile Arg Thr Ser Gly Val Val Thr
 290                 295                 300

Ser Cys Thr Gly Val Leu Pro Gln Leu Ser Met Val Lys Tyr Asn Cys
305                 310                 315                 320

Asn Lys Cys Asn Phe Val Leu Gly Pro Phe Cys Gln Ser Gln Asn Gln
            325                 330                 335

Glu Val Lys Pro Gly Ser Cys Pro Glu Cys Gln Ser Ala Gly Pro Phe
            340                 345                 350

Glu Val Asn Met Glu Glu Thr Ile Tyr Gln Asn Tyr Gln Arg Ile Arg
            355                 360                 365

Ile Gln Glu Ser Pro Gly Lys Val Ala Ala Gly Arg Leu Pro Arg Ser
 370                 375                 380
```

-continued

```
Lys Asp Ala Ile Leu Leu Ala Asp Leu Val Asp Ser Cys Lys Pro Gly
385                 390                 395                 400

Asp Glu Ile Glu Leu Thr Gly Ile Tyr His Asn Asn Tyr Asp Gly Ser
            405                 410                 415

Leu Asn Thr Ala Asn Gly Phe Pro Val Phe Ala Thr Val Ile Leu Ala
        420                 425                 430

Asn His Val Ala Lys Lys Asp Asn Lys Val Ala Val Gly Glu Leu Thr
    435                 440                 445

Asp Glu Asp Val Lys Met Ile Thr Ser Leu Ser Lys Asp Gln Gln Ile
450                 455                 460

Gly Glu Lys Ile Phe Ala Ser Ile Ala Pro Ser Ile Tyr Gly His Glu
465                 470                 475                 480

Asp Ile Lys Arg Gly Leu Ala Leu Ala Leu Phe Gly Gly Glu Pro Lys
            485                 490                 495

Asn Pro Gly Gly Lys His Lys Val Arg Gly Asp Ile Asn Val Leu Leu
        500                 505                 510

Cys Gly Asp Pro Gly Thr Ala Lys Ser Gln Phe Leu Lys Tyr Ile Glu
    515                 520                 525

Lys Val Ser Ser Arg Ala Ile Phe Thr Thr Gly Gln Gly Ala Ser Ala
530                 535                 540

Val Gly Leu Thr Ala Tyr Val Gln Arg His Pro Val Ser Arg Glu Trp
545                 550                 555                 560

Thr Leu Glu Ala Gly Ala Leu Val Leu Ala Asp Arg Gly Val Cys Leu
            565                 570                 575

Ile Asp Glu Phe Asp Lys Met Asn Asp Gln Asp Arg Thr Ser Ile His
        580                 585                 590

Glu Ala Met Glu Gln Gln Ser Ile Ser Ile Ser Lys Ala Gly Ile Val
    595                 600                 605

Thr Ser Leu Gln Ala Arg Cys Thr Val Ile Ala Ala Asn Pro Ile
610                 615                 620

Gly Gly Arg Tyr Asp Pro Ser Leu Thr Phe Ser Glu Asn Val Asp Leu
625                 630                 635                 640

Thr Glu Pro Ile Ile Ser Arg Phe Asp Ile Leu Cys Val Val Arg Asp
            645                 650                 655

Thr Val Asp Pro Val Gln Asp Glu Met Leu Ala Arg Phe Val Val Gly
        660                 665                 670

Ser His Val Arg His His Pro Ser Asn Lys Glu Glu Gly Leu Ala
    675                 680                 685

Asn Gly Ser Ala Ala Glu Pro Ala Met Pro Asn Thr Tyr Gly Val Glu
690                 695                 700

Pro Leu Pro Gln Glu Val Leu Lys Lys Tyr Ile Ile Tyr Ala Lys Glu
705                 710                 715                 720

Arg Val His Pro Lys Leu Asn Gln Met Asp Gln Asp Lys Val Ala Lys
            725                 730                 735

Met Tyr Ser Asp Leu Arg Lys Glu Ser Met Ala Thr Gly Ser Ile Pro
        740                 745                 750

Ile Thr Val Arg His Ile Glu Ser Met Ile Arg Met Ala Glu Ala His
    755                 760                 765

Ala Arg Ile His Leu Arg Asp Tyr Val Ile Glu Asp Val Asn Met
770                 775                 780

Ala Ile Arg Val Met Leu Glu Ser Phe Ile Asp Thr Gln Lys Phe Ser
785                 790                 795                 800

Val Met Arg Ser Met Arg Lys Thr Phe Ala Arg Tyr Leu Ser Phe Arg
```

```
                    805                 810                 815
Arg Asp Asn Asn Glu Leu Leu Leu Phe Ile Leu Lys Gln Leu Val Ala
                820                 825                 830

Glu Gln Val Thr Tyr Gln Arg Asn Arg Phe Gly Ala Gln Gln Asp Thr
            835                 840                 845

Ile Glu Val Pro Glu Lys Asp Leu Val Asp Lys Ala Arg Gln Ile Asn
        850                 855                 860

Ile His Asn Leu Ser Ala Phe Tyr Asp Ser Glu Leu Phe Arg Met Asn
865                 870                 875                 880

Lys Phe Ser His Asp Leu Lys Arg Lys Met Ile Leu Gln Gln Phe Leu
                885                 890                 895

Glu Asp Tyr Lys Asp Asp Asp Lys
            900                 905

<210> SEQ ID NO 14
<211> LENGTH: 10
<212> TYPE: PRT
<213> ORGANISM: Artificial Sequence
<220> FEATURE:
<223> OTHER INFORMATION: Amino acid sequence for the MCM2 epitope of
      monoclonal antibody 26H6.19 (refined)

<400> SEQUENCE: 14

His Val Arg His His Pro Ser Asn Lys Glu
1               5                   10
```